United States Patent [19]
Hustad et al.

[11] Patent Number: 6,087,122
[45] Date of Patent: *Jul. 11, 2000

[54] HUMAN E3 UBIQUITIN PROTEIN LIGASE

[75] Inventors: Carolyn Marziasz Hustad, Wilmington, Del.; Namit Ghildyal, Kennett Square, Pa.

[73] Assignee: Zeneca Limited, London, United Kingdom

[ * ] Notice: This patent is subject to a terminal disclaimer.

[21] Appl. No.: 09/357,746

[22] Filed: Jul. 21, 1999

Related U.S. Application Data

[63] Continuation-in-part of application No. 09/070,060, Apr. 30, 1998, Pat. No. 5,976,849
[60] Provisional application No. 60/073,839, Feb. 5, 1998.

[51] Int. Cl.[7] .......................... C07H 21/04; C12N 15/00; C12N 5/00; C12Q 1/02
[52] U.S. Cl. .......................... 435/29; 435/320.1; 435/325; 435/375; 536/23.2; 536/24.5
[58] Field of Search ................................. 536/23.1, 23.2, 536/23.5, 24.5; 435/6, 320.1, 325, 455, 183, 29, 375

[56] References Cited

PUBLICATIONS

Sigma Catalog, 1990, p 815 & 617.
Hochstrasser, Mark; Ubiquitin–Dependent Protein Degradation, *Annu. Rev. Genet.* 1996, 30:405–39.
Weissman, Alan M.; Regulating Protein Degradation by Ubiquitination, *Review Immunology Today*, vol. 18, No. 4 189, Apr. 1997.
Pahl, Heike L. et al.; Control of Gene Expression by Proteolysis, *Current Opinion in Cell Biology* 1996, 8:340–347.
Rolfe, Mark et al.; The Ubiquitin–Mediated Proteolytic Pathway as a Therapeutic Area, *J. Mol. Med.* (1997) 75:5–17.
Perry, William L. et al.; The Itchy Locus Encodes a Novel Ubiquitin Protein Ligase That is Disrupted in a $18^h$ Mice, *Nature Genetics*, vol. 18, Feb. 1998.
D'Andrea, Alan D., Relieving the Itch, *Nature Genetics*, vol. 18, Feb. 1998.
Wood, Jonathan D. et al.; Atrophin–1, the DRPLA Gene Product, Interacts with Two Families of WW Domain–Containing Proteins; *Molecular and Cellular Neuroscience* 11, 149–160 (1998), Article No. CN980677.

*Primary Examiner*—George C. Elliott
*Assistant Examiner*—Karen A Lacourciere
*Attorney, Agent, or Firm*—Patrick H. Higgins, Esq.

[57] ABSTRACT

Human E3 ubiquitin protein ligase is described. A structural region which encodes the polypeptide is disclosed as well as the the amino acid residue sequence of the protein ligase. Methods are provided which employ the sequences to identify compounds that modulate a biological and/or pharmacological activity of the molecule and hence regulate cellular and tissue physiology. The invention is also drawn toward the diagnosis, prevention, and treatment of pathophysiological disorders mediated by E3 ubiquitin protein ligases.

12 Claims, 5 Drawing Sheets

Human Itchy E3 Ubiquitination Assays

| − | + | + | + | − | − | E1 |
|---|---|---|---|---|---|---|
| − | + | + | − | + | − | E2 | (UbcH7)
| − | GST | GST–E3 | | | | E3 | kDa

HUMAN E3 UBIQUITIN PROTEIN LIGASE

This is a 37 CFR 53(b) Continuation in Part Application wherein priority is claimed under 35 USC § 120 from U.S. application Ser. No.09/070,060, filed Apr. 30, 1998 now U.S. Pat. No. 5,976,849 in which priority is claimed under 35 USC § 119(e) from U.S. Provisional Application Ser. No. 60/073,839, filed Feb. 5, 1998; the entire disclosures of which are each incorporated by reference.

FIELD OF THE INVENTION

The present invention relates to nucleic acid and amino acid sequences of E3 ubiquitin protein ligase and to the use of these sequences to identify compounds that modulate the biological activity of the native biomolecule as well as modulate protein degradation or selective proteolysis and/or otherwise modulate physiological conditions associated with aberrant ubiquitin dependent proteolysis in human physiology.

BACKGROUND OF THE INVENTION

Three major proteolytic pathways (lysosomal, calcium-dependent, and the ATP-dependent pathways) exist in eukaryotic cells. The ATP-dependent pathway has long been known orchestrate specific degradation of native proteins. Recently it has become clear that the ATP-dependent ubiquitin mediated intracellular pathway is responsible for selective degradation of intact biomolecules as an efficiently evolved mechanism to adapt cellular physiology to the needs of the organism. Proteolysis is a powerful means of regulation due to the speed and irreversibility which enables the cell to rapidly eliminate or reduce the functional level of a particular biological molecule. See, e.g., Jentsch, S., et al., *Selective Protein Degradation: A Journey's end Within the Proteasome*, Cell, 82:129 (1995). The critical role of ubiquitin-dependent proteolysis has steadily become increasingly clear, for example, in the normal degradation of oncoproteins and tumor suppressers in cell cycle control as well as in stress response and the immune system. Hochstrasser, M., Current Biology, 4:1024 (1992); Deshaies, R. J., Trends Cell Biol., 5:428 (1995); Hilt, W., et al., Trends Biol. Sci., 21:96 (1996).

Ubiquitin is a heat-stable 76-amino acid biomolecule considered to be the most highly conserved protein known. Selective protein degradation via the ubiquitin pathway generally involves tagging of the target protein (substrate) by covalent attachment of multiple molecules of ubiquitin, and degradation of the target by the 26 S proteasome complex. Proteins are marked for direction to the proteasome via the covalent addition of branched polyubiquitin chains to the ax-amino group of one or more surface lysines. The amide linkage of ubiquitin to a substrate protein is generally carried out by three classes of accessory enzymes in a sequential reaction. Ubiquitin activating enzymes (E1) activate ubiquitin by forming a high energy thiol ester intermediate. Activation of the C-terminal Gly of ubiquitin by E1, is followed by the activity of a ubiquitin conjugating enzyme E2 which serves as a carrier of the activated thiol ester form of ubiquitin during the transfer of ubiquitin directly to the third enzyme, E3 ubiquitin protein ligase. E3 ubiquitin protein ligase is responsible for the final step in the conjugation process which results in the formation of an isopeptide bond between the activated Gly residue of ubiquitin, and an α-NH group of a Lys residue in the substrate or a previously conjugated ubiquitin moiety. See, e.g., Hochstrasser, M., *Ubiquitin-Dependent Protein Degradation*, Annu. Rev. Genet., 30:405 (1996).

In a reconstituted system, for example, all three categories of affinity purified enzymes (E1, E2, and E3) are required for the breakdown of $^{125}$I-albumin to acid-soluble material in the presence of ubiquitin and ATP. Sears, C., et al., NF-kB p105 *Processing Via the Ubiquitin-Proteasome Pathway*, J Biol Chem., 273:1409 (1998). The high specificity of the ubiquitin selective-destruction pathway is predicted to allow the development of new classes of highly potent and selective low molecular weight enzyme inhibitors targeting particular members of the ubiquitin pathway that control the intracellular levels of a wide range of important regulatory proteins. Rolfe, M., et al., *The Ubiquitin-Mediated Proteolytic Pathway as a Therapeutic Area*, J. Mol. Med. 75:5–17 (1997).

Compelling evidence has been presented that implicates ubiquitination in the turnover of the tumor supressor protein, p53, cell cycle regulators cyclin A and cyclin B, the kinase c-mos, the cystic fibrosis transmembrane conductance regulator, the DNA repair protein $O^6$-methylguanine-DNA methyl transferase, the transcriptional co-activator p300, the transcription factors c-jun, c-fos, IκB/NFκB, the transcription factors c-myc, DP1, and E2F, the regulatory subunit of cAMP-dependent protein kinase, receptors for peptide growth factors, estradiol receptor, as well as oncoprotein E1A. Moreover, as a corollary, pharmacological intervention which alters the half-lives of these cellular proteins is expected to have significant value in wide therapeutic potential, particularly in the areas of autoimmune disease, inflammation, cancer, as well as other proliferative disorders. Rolfe, M., et al., *The Ubiquitin-Mediated Proteolytic Pathway as a Therapeutic Area*, J. Mol. Med., 75:5 (1997).

E3 ubiquitin protein ligase, as the final player in the ubiquitination process, is responsible for target specificity of ubiquitin-dependent proteolysis. A number of E3 ubiquitin-protein ligases have previously been identified. See, e.g., D'Andrea, A. D., et al., Nature Genetics, 18:97 (1998); Gonen, H., et al., *Isolation, Characterization, and Purification of a Novel Ubiquitin-Protein Ligase, E3-Targeting of Protein Substrates via Multiple and Distinct Recognition Signals and Conjugating Enzymes*, J. Biol. Chem., 271:302 (1996); Scheffner, M., et al., *The HPV-16 E6 and E6-AP Complex Functions as a Ubiquitin-Protein Ligase in the Ubiquitination of p53*, Cell, 75:495 (1993); Huibregtse, J. M., et al., *A Family of Proteins Structurally and Functionally Related to the E6-AP Ubiquitin Protein Ligase*, PNAS, 92:2563 (1995); Staub, O., et al., *WW Domains of Nedd4 Bind to the Proline-Rich PY Motifs in the Epithelial Na+ Channel Deleted in Liddles Syndrome*, EMBO, 15:2371 (1996) [the substrate specificity is determined by the E3 ligase]; Siepmann, T. J., et al., *Evidence for Stable, Exchangeable E1/E2/E3 Ubiquitin Conjugation Complexes at Physiological Concentrations*, FASEB J., 10:2324 (1996).

Other E3 ligases have been extensively evaluated in *S. cerevisiae* and in cell-free systems using engineered proteins as test substrates. Weissman, A. M., *Regulating Protein Degradation by Ubiquitination*, Review Immunology Today, 18(4): 189 (1997); Sudakin, V., et al., Mol. Biol. Cell, 6:185 (1995); Stancovski, I., et al., Mol. Cell. Biol., 15:7106 (1995); King, R. W., et al., Cell, 81:279 (1995); Chen, Z. J., et al., Cell, 84:853 (1996); Orian, A., et al., J. Biol. Chem., 170:21707 (1995); Varshavsky, A., etal., Cell, 69:725 (1992); Hershko, A., et al., Annu. Rev. Biochem., 61:761 (1992); Ciechanover, A., Cell, 7:13 (1994).

Perry et al., recently identified a single gene which encodes a murine E3 ubiquitin protein ligase of the Hect family, disruption of which is demonstrated to cause an inflammatory phenotype of the mouse as well as enhanced epithelial and haematopoietic cell growth. Perry, W. L., et al., Nature Genetics, 18:143 (1998). The murine E3 results reported by Perry et al indicate the specific ubiquitin-dependent proteolysis is an important mediator in the immune response as well as haematopoietic cell growth in vivo. Moreover, it is recently set forth that modulators of the E3 ubiquitin protein ligase are likely to have significant therapeutic potential, inter alia, as novel anti-inflammatory agents as well as entities to promote wound-healing. D'Andrea, A. D., et al., Nature Genetics, 18:97 (1998); Perry, W. L., etal., Nature Genetics, 18:143 (1998).

However, the previously reported E3 ubiquitin protein ligase is a murine isolate. The availability of an analogous functional human homolog will be ideal for the identification of compounds which modulate the specific biological activity of the E3 protein ligase and, as a corollary, modulate the physiological conditions associated with aberrant ubiquitin dependent proteolysis in human physiology. The availability of an analogous functional human homolog will also be ideal for the diagnosis, study, prevention, and treatment of pathophysiological disorders related to the biological molecule.

SUMMARY OF THE INVENTION

The present invention is directed toward a polynucleotide which comprises a nucleic acid sequence which encodes a E3 ubiquitin protein ligase polypeptide comprising an amino acid sequence having at least about 80% homology to SEQ ID NO:3 and comprising at least one amino acid, relative to the position of SEQ ID NO:3, selected from the group consisting essentially of(V66, H70, A89, V108, G113, I122, I127, L134, S136, T145, A150, S151, S157, S159, K160, E162, D171, D175, G177, A178, R182, V184, S185, A225, T226, E228, N245, P271, T273, S380, T452, D650, and A752) and/or wherein cysteine at position 820 (C820), relative to SEQ ID NO:3, is substituted or deleted.

The present invention is also directed to an isolated and purified polynucleotide molecule, which comprises a nucleic acid sequence which encodes a E3 ubiquitin protein ligase polypeptide comprising an amino acid sequence having at least about 96% homology to SEQ ID NO:3. A preferred embodiment of the present invention is a polynucleotide which comprises a nucleic acid sequence which encodes a E3 ubiquitin protein ligase polypeptide comprising an amino acid sequence having at least about 96% homology to SEQ ID NO:3 and comprising at least one amino acid, relative to the position of SEQ ID NO:3, selected from the group consisting essentially of (V66, H70, A89, V108, G113, I122, I127, L134, S136, T145, A150, S151, S157, S159, K160, E162, D171, D175, G177, A178, R182, V184, S185, A225, T226, E228, N245, P271, T273, S380, T452, D650, and A752).

The invention is also directed to an antisense molecule which is derived from and complementary to SEQ ID NO:1.

The invention is further directed to a method of identifying a compound that modulates a biological and/or pharmacological activity of an E3 ubiquitin protein ligase polypeptide which is encoded by a polynucleotide of the present invention, comprising:

combining a candidate compound modulator with the polypeptide and measuring an effect of the candidate compound modulator on the biological and/or pharmacological activity of the polypeptide.

The invention is further directed to a method of modulating a biological and/or pharmacological activity of a E3 ubiquitin protein ligase polypeptide in a cell comprising administering an effective amount of a polynucleotide of the present invention to said cell—or—an effective amount of compound identified by means of a method of the present invention.

BRIEF DESCRIPTION OF THE FIGURES

FIG. 2 demonstrates the recombinant human E3 ubiquitin ligase (SEQ ID NO:3) has ubiquitinating activity in vitro.

DETAILED DESCRIPTION OF THE INVENTION

Figure 1:
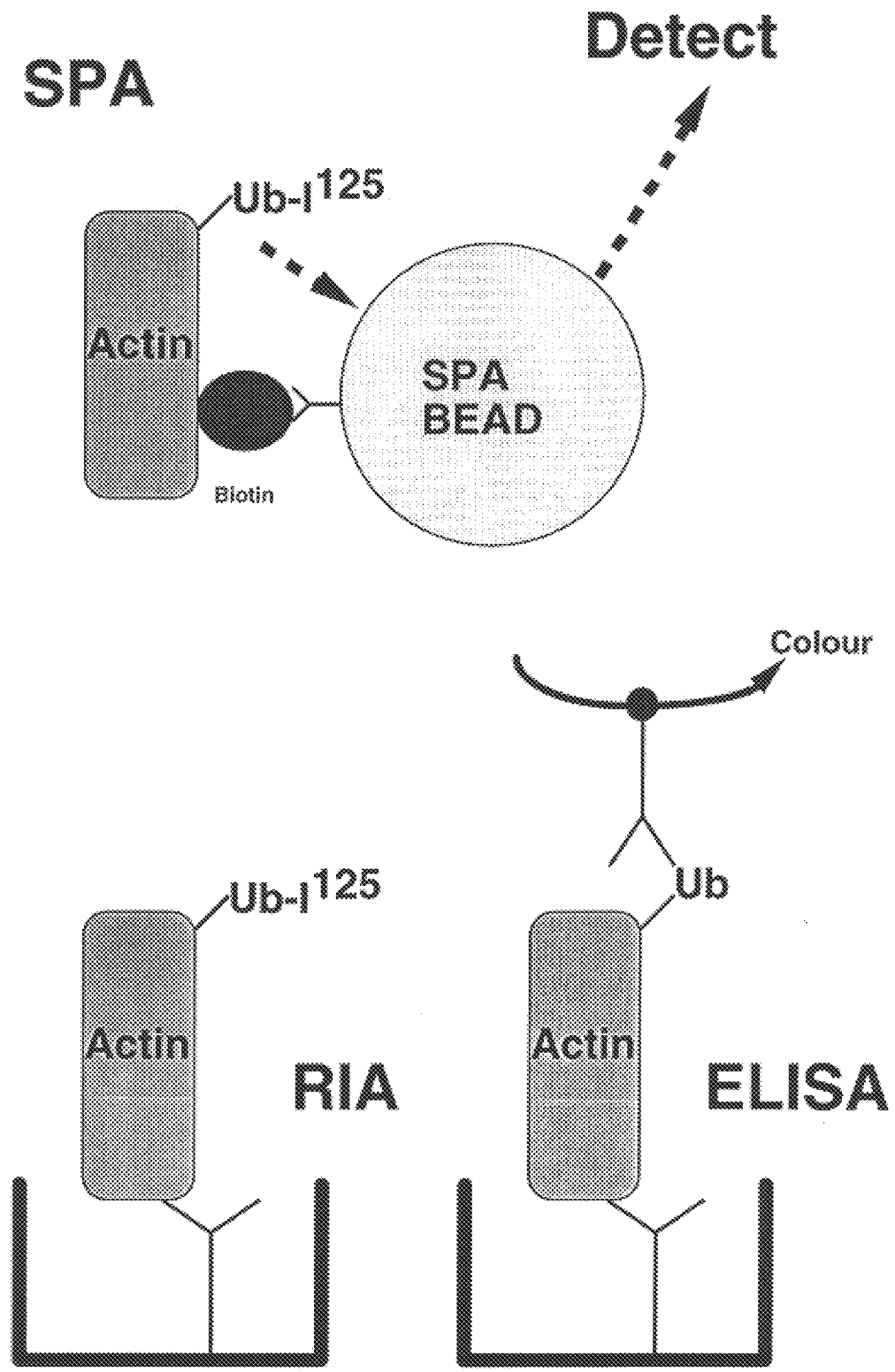
FIG. 1 shows a schematic representation of example Scintillation Proximity Assays (SPA), as well as RIA and ELISA Assays.

Unless defined otherwise, all technical and scientific terms used herein have the same meaning as is commonly understood by one of skill in the art to which this invention belongs. All publications and patents referred to herein are incorporated by reference.

Nucleic acid sequence as used herein refers to an oligonucleotide, nucleotide or polynucleotide sequence, and fragments or portions thereof, and to DNA or RNA of genomic or synthetic origin which may be double-stranded or single-stranded whether representing the sense or antisense strand. Similarly, amino acid and/or residue sequence as used herein refers to peptide or protein sequences or portions thereof.

Biological activity as used herein refers to the ability of the novel human E3 ubiquitin protein ligase and variations thereof contemplated herein to bind ubiquitin and/or transfer ubiquitin to a substrate under biological conditions.

Pharmacological activity, as used herein in reference to the novel human E3 ubiquitin protein ligase and variations thereof contemplated herein, refers to the ability to modulate protein degradation or selective proteolysis and/or otherwise modulate physiological conditions associated with aberrant ubiquitin dependent proteolysis in human physiology discussed infra.

'Relative to the position of SEQ ID NO:3' as used herein is used to designate amino acid positions that correspond to the respective 852 amino acid residue positions of SEQ ID NO:3 or a subgroup thereof. For example SEQ ID NO:4, the 854 amino acid sequence of the murine E3 ubiquitin protein ligase, displays two 'insertion' amino acids which are not present in the human SEQ ID NO:3. The 'insertion' amino acids, at positions 244 and 245 of SEQ ID NO:4, designated D244, D245, do not correspond to SEQ ID NO:3. In this example, positions 1-243 and 246-854 are therefore defined as being 'relative to SEQ ID NO:3'. Similarly embodiments may be generated from SEQ ID NO:3 which manifest truncations and/or deletions but retain amino acids relative to the position of SEQ ID NO:3, particularly at least one amino acid, relative to the position of SEQ ID NO:3, selected from the group consisting essentially of (V66, H70, A89, V108, G113, I122, I127, L134, S136, T145, A150, S151, S157, S159, K160, E162, D171, D175, G177, A178, R182, V184, S185, A225, T226, E228, N245, P271, T273, S380, T452, D650, and A752).

Dominant negative mutant as used herein refer to a nucleic acid coding region sequence which has been changed with regard to at least one position in the sequence, relative to the corresponding wild type native version, preferably at a position which changes an amino acid residue position at an active site required for biological and/or pharmacological activity in the native peptide to thereby encode a mutant peptide. Dominant negative mutant embodiments of the invention, for example, include a peptide comprising a sequence as depicted in SEQ ID NO:3 or a peptide having at least about 80% homology to SEQ ID NO:3 and at least one amino acid, relative to the position of SEQ ID NO:3, selected from the group consisting essentially of (V66, H70, A89, V 108, G 113, I122, I127, L134, S136, T145, A150, S151, S157, S159, K160, E162, D171, D175, G177, A178, R182, V184, S185, A225, T226, E228, N245, P271, T273, S380, T452, D650, and A752). wherein cysteine at position 820 (C820) is substituted or deleted. Dominant negative mutants are moreover defined to be included within the scope of the disclosure of the variants section infra.

The term 'modulation' is used herein to refer to the capacity to either enhance or inhibit the biological activity of a E3 ubiquitin protein ligase. The term "modulation" is also used herein to refer to the pharmacological capacity to to either enhance or inhibit the selective elimination of a biological protein molecule via ubiquitin dependent proteolysis under biological conditions.

As used herein, a functional derivative of a biomolecule disclosed herein is an entity that possesses a functional biological activity and/or pharmacological activity as defined herein that is derived from SEQ ID NO:1 or SEQ ID NO:3, for example, truncated versions, versions having deletions, functional fragments, versions having substitutions, versions having insertions or extended ends, or biologically effective dominant negative mutants as well as biologically effective antisense molecules.

Substantially as depicted as used herein refers to functional derivative proteins, and functional derivative nucleic acid sequences as defined herein that may have changes but perform substantially the same biochemical or pharmacological function in substantially the same way; however, 'substantially as depicted' as used herein also refers to biologically effective dominant negative mutants and is intended to encompass biologically effective antisense molecules as defined herein.

Biologically effective as used herein in reference to antisense nucleic acid molecules as well as dominant negative mutant nucleic acid coding regions and dominant negative mutant peptides refers to the ability of these molecules to modulate the biological activity and/or pharmacological activity of the E3 ubiquitin protein ligase of the present invention and/or transcription/translation of nucleic acid coding regions of the protein ligase of the present invention.

Direct administration as used herein refers to the direct administration of nucleic acid constructs which encode embodiments (e.g., SEQ ID NO:3, dominant/negative mutant version, antisense molecule, antibody molecule, modulator compound molecule) of the present invention or fragments thereof; and the direct administration of embodiments of the present invention or fragments thereof, and the in vivo introduction of molecules of the present invention preferably via an effective eukaryotic expression vector in a suitable pharmaceutical carrier. Polynucleotides and therapeutic molecules of the present invention may also be delivered in the form of nucleic acid transcripts.

Ubiquitin-Dependent Proteolysis

Ubiquitination has recently become a focal point in cell biology as it is acknowledged in joining phosphorylation as a major protein modification device in regulation of cell physiology. The importance of ubiquitin-dependent proteolysis for selective elimination of biomolecules is indisputable for the maintenance of cellular integrity and physiology of the organism. The depth of current knowledge about the molecular mechanisms regulating ubiquitin-dependent proteolysis, combined with the understanding of how impairment of such processes, underlies pathological conditions, has opened the way for a mechanism-based approach for the development of new drugs. Rolfe, M., et al., *The Ubiquitin-Mediated Proteolytic Pathway as a Therapeutic Area*, J. Mol. Med. 75:5–17 (1997).

A growing number of cellular regulatory mechanisms are being linked to ubiquitin. For instance, ubiquitination is a widely utilized ligand-mediated means of modulating transmembrane receptor function. Mammalian transmembrane receptors found to undergo ligand-mediated ubiquitination are coupled to, or are themselves, tyrosine kinases. Ubiquitination of the T-cell receptor (TCR) is stimulated by antigen (MHC and peptide), superantigens, lectins that bind the TCR, or by anti-receptor antibodies. Moreover, correlations between dysregulated ubiquitination/proteasomal degradation and cellular transformation are striking. Weissman, A. M., *Regulating Protein Degradation by Ubiquitination*, Review Immunology Today, 18(4):189 (1997).

Ubiquitination is now implicated in regulating numerous cellular processes including: signal transduction, cell-cycle progression, receptor-mediated endocytosis, transcription (including activation-induced transcription in lymphocytes), organelle biogenesis and spermatogenesis. Abnormal accumulations of ubiquitinated species are found in intracellular inclusions in neuropathological conditions including Alzheimer's and Pick's diseases. The importance of regulated ubiquitination is demonstrated by the resistance of oncogenic counterparts of normal cellular ubiquitination substrates to this post-translational modification, and by correlations between malignant transformation and loss of function, or dysregulated function, of enzymes involved in ubiquitination. Proteasomes have recently been implicated in programmed cell death in neurons and thymocytes at points proximinal to activation of the interleukin-1β-converting enzyme (ICE) family of proteases. Morover, dysregulated ubiquitination contributes to malignant transformation, for example, oncogenic counterparts of normally ubiquitinated proteins are resistant to ubiquitination. Weissman, A. M., *Regulating Protein Degradation by Ubiquitination, Review Immunology Today*, 18(4): 189 (1997); Papavassiliou, A. G., et al., Science, 258:1941 (1992); Treier, M., et al., Cell, 78:787 (1994); Papa, F. R., etal., Nature, 366:319 (1993); Grimm, L. M., et al., EMBO, 15:3835 (1996); Sadoul, R., et al., EMBO, 15:3845 (1996).

E3 Ligase

Ubiquitin-dependent proteolysis needs to be very selective in order to effectively regulate intracellular physiology. The component of the ubiquitin conjugation system generally believed to be the most directly involved in substrate recognition is the E3 protein ligase. See, e.g., Hochstrasser, M., *Ubiquitin-Dependent Protein Degradation*, Annu. Rev. Genet., 30:405 (1996). The first E3 ligase to be identified, E6-AP, is the best previously characterized member of the Hect-domain class. E6-AP was originally identified through its interaction with the E6 oncoprotein of the cancer-associated human papillomavirus types 16 and 18. The E6/E6-AP complex specifically binds to the tumor suppressor protein p53 and induces its ubiquitination and subsequent degradation. The cysteine residue necessary for thioester formation of E6-AP with ubiquitin is conserved among all of the Hect-domain class proteins. Because of this similarity these proteins have been termed Hect proteins, for 'Homologous to E6-AP C Terminus' (HECT).

An essential intermediate step in E6-AP-dependent protein ubiquitination is the formation of a thioester complex between ubiquitin and E6-AP. Furthermore, the direction of ubiquitin transfer is from E1 to E2 and then from E2 to E6-AP. This suggests that in this particular system, the E3 catalyzes the final attachment of ubiquitin to a substrate protein, rather than the E2 as shown for few other systems. The cysteine residue of E6-AP involved in thioester formation has been mapped to the carboxyl terminus. The carboxyl-terminal regions of several proteins from different organisms show significant similarity to the carboxyl terminus of E6-AP.

Furthermore, another ubiquitin protein ligase (E3) has been characterized as the neuronal precursor cell-expressed developmentally downregulated 4 (Nedd4). The biological structure is a multimodular protein composed of a C2 domain, 3 (or 4) WW domains, and a C-terminal ubiquitin protein ligase Hect domain. Nedd4 is a protein that interacts with the epithelial Na+channel (ENaC) which is mediated by an association of the WW domains of Nedd4 with the proline-rich PY motifs (XPPXY, where X=any amino acid) of the ENaC subunits. Deletion or mutations within the PY motifs of the ENaC subunits have been genetically linked to Liddle syndrome, a hereditary form of systemic renal hypertension caused by an abnormal increase in ENaC activity. Recent work has described interaction of Nedd4 and Nedd4-like proteins with other PY motif-containing proteins, also mediated by the WW domains wherein the substrate specificity is determined by the E3 ligase. Staub, O.,et al., EMBO, 15:2371 (1996).

Human E3 Ubiquitin Protein Ligase

The human E3 ligase described herein is a member of the Hect-domain containing ubiquitin-protein ligases, named for the highly conserved C-terminal portion of the molecule. SEQ ID NO:1 is a 5372 base cDNA nucleic acid sequence which encodes the novel human E3 ubiquitin protein ligase described herein. SEQ ID NO:2 is a 2559 base translated structural coding region of the cDNA nucleic acid sequence which encodes the novel human E3 ubiquitin protein ligase. SEQ ID NO:3 is a 852 amino acid residue sequence of the human E3 ubiquitin protein ligase homolog described herein. SEQ ID NO:4, for comparison, is the 854 amino acid residue sequence of the murine E3 ubiquitin protein ligase mapped to 'itchy' locus as described by Perry, W. L., et al., Nature Genetics, 18:143 (1998); Hustad, C. M., et al., Genetics, 140:255 (1995).

The native human protein (SEQ ID NO:3) is 95.9% homologous to the murine 'itchy' E3 ubiquitin ligase (SEQ ID NO:4), at the amino acid level. The murine polypeptide has two 'insertion' amino acids, relative to SEQ ID NO:3, at positions 244 and 245 of SEQ ID NO:4. Example amino acid positions which are characteristic of and unique to the human molecule, SEQ ID NO:3, are V66, H70, A89, V108, G113, I122, I127, L134, S136, T145, A150, S151, S157, S159, K160, E162, D171, D175, G177, A178, R182, V184, S185, A225, T226, E228, N245, P271, T273, S380, T452, D650, and A752. These characteristic amino acid positions are believed to be 'humanizing' amino acids which each particularly distinguish the human E3 ubiquitin ligase from the murine molecule. Moreover, each one, in part and in sum, confer biophysical properties which are characteristic of the human molecule described herein. Therefore molecules of the invention are particularly preferred which comprise an amino acid sequence having at least about 96% homology to SEQ ID NO:3 and comprising at least one amino acid, relative to the position of SEQ ID NO:3, selected from the group consisting essentially of (V66, H70, A89, V108, G113, I122, I127, L134, S136, T145, A150, S151, S157, S159, K160, E162, D171, D175, G177, A178, R182, V184, S185, A225, T226, E228, N245, P271, T273, S380, T452, D650, and A752). Example embodiments of the invention contemplated herein therefore include SEQ ID NO:4 wherein one or more of the following changes are made, relative to SEQ ID NO:3: V66, H70, A89, V108, G113, I122, I127, L134, S136, T145, A150, S151, S157, S159, K160, E162, D171, D175, G177, A178, R182, V184, S185, A225, T226, E228, N245, P271, T273, S380, T452, D650, and A752.

The conserved cysteine residue where a ubiquitin linkage is expected to occur is apparent at position 820 of SEQ ID NO:3. This residue position is of particular significance especially for the construction of pharmacologically valuable dominant negative mutants. See, Example VIII. The novel human E3 recombinant enzyme described herein, e.g., SEQ ID NO:3, is expected to have inherently high native catalytic activity. Moreover, any change (e.g., substitution or deletion) to the residue where ubiquitin linkage is expected to occur (SEQ ID NO:3, cysteine position 820; SEQ ID NO:4 cysteine position 822) is expected to be significantly compromise the catalytic activity of the E3 ubiquitin protein ligase.

The 'itchy' mice (murine E3 ligase knockout) display a phenotype that suggests activation of processes typical of chronic inflammatory and/or wound healing events, including lymphoid hyperplasia and hematopoietic cell proliferation further discussed infra. In order to evaluate the role of SEQ ID NO:3 E3 ligase in the activation of human leukocytes, stimulation experiments were performed independently using peripheral blood mononuclear cells, Jurkat cells, and U937 cells. See, Example IX. Following stimulation, cells were collected by low-speed centrifugation and lysed to isolate either protein for Western blot analysis (FIG. 4) or RNA for Northern blot analysis (FIG. 5). Proteins were transferred to nitrocellulose membranes, immunoblotted using an anti-peptide antibodies described herein and a horseradish peroxidase-conjugated anti-rabbit secondary antibody. A marked decline is demonstrated in the intracellular SEQ ID NO:3 levels 2 h after activation of the jurkat T cells. Activation of T lymphocytes by PMA and ionomycin results in a signal transduction cascade; the findings demonstrated herein indicate that the SEQ ID NO:3 'itchy' E3 ligase is involved in turnover of signal transduction proteins in the lymphocytic cells. See, FIG. 4. The results demonstrate that the human itchy E3 ligase mRNA levels dramatically decline within 3 h after stimulation of PBMC's. These results suggest that the 'itchy' E3 ligase gene is involved in turnover of signal transduction molecules in the hematopoietic lineages. See, FIG. 5.

Chromosomal Location

The E3 ligase gene (SEQ ID NO:1) has been mapped to human chromosome 20q11.23-12 using the Stanford G3 radiation hybrid panel. The most proximal markers are SHGC 53176, SHGC 8755, and SHGC 2765.

Substrate

The novel human E3 ubiquitin protein ligase (e.g., SEQ ID NO:3) ubiquitinates specific intracellular biological molecules in vivo to effect selective destruction and swift regulation of cellular physiology. Biological activity refers to the ability of the novel human E3 ubiquitin protein ligase and variations thereof contemplated herein to bind ubiquitin and/or transfer ubiquitin to a substrate under biological conditions. Substrates include the likes of intracellular messenger biological molecules, receptors, ligands, signal transduction molecules, transcriptional activators, cytokines, kinases, phosphatases and phosphorylases, especially which mediate physiological conditions such as inflammation, autoimmune disease, neurological disease, apoptosis, endothelial cell physiology (e.g., proliferation, differentiation), peripheral vascular disease, angiogenesis, cancer, anemia, hematopoietic disorders, cachexia, leukemia, pulmonary disorders, arthritis, diabetes, and viral infection. Pharmacological activity, as used herein in reference to the novel human E3 ubiquitin protein ligase (e.g., SEQ ID NO:3) and variations thereof contemplated herein, refers to the ability to modulate protein degradation or selective proteolysis and/or otherwise modulate physiological conditions associated with aberrant ubiquitin dependent proteolysis in human physiology (e.g., disorders manifested by aberrant forms and/or abnormal levels of the native E3 ubiquitin protein ligase).

Pharmacological Significance

The control of hematopoiesis is a highly regulated process that responds to a number of physiological stimuli in the human body. Differentiation, proliferation, growth arrest, or apoptosis of blood cells depends on the presence of appropriate cytokines and their receptors, as well as the corresponding cellular signal transduction cascades. Hu, Mickey C.-T., et al., Genes & Development, 10:2251(1996). Generation of mature leukocytes, for instance, is a highly regulated process which responds to various environmental and physiological stimuli. Cytokines cause cell proliferation, differentiation or elimination, each of these processes being dependent on the presence of appropriate cytokine receptors and the corresponding signal transduction elements. Moreover, the stimulation of quiescent B- and T-lymphocytes occur via antigen receptors which exhibit remarkable homology to cytokine receptors. Grunicke, Hans H., *Signal Transduction Mechanisms in Cancer,* Springer-Verlag (1995). See also, Suchard, S. J., et al., *Mitogen-Activated Protein Kinase Activation During IgG-Dependent Phagocytosis in Human Neutrophils,* J. Immunol., 158:4961 (1997).

The identification of a single gene underlying an inflammatory syndrome provides significant potential to identify novel targets for anti-inflammatory drugs, inter alia. Modulators of the human E3 ubiquitin protein ligase described herein accordingly have significant potential as novel anti-inflammatory agents as well as agents to promote wound-healing. See, D'Andrea, A. D., etal., Nature Genetics, 18:97 (1998). Moreover, compounds which modulate the biological activity of the human E3 ubiquitin protein ligase in vivo are expected to to influence hematopoiesis. The 'itchy' knockout mice (murine E3 ubiquitin protein ligase (SEQ ID NO:4)) have demonstrated enhanced hematopoiesis, manifested, for example, by accelerated development of the erythroid, myeloid, and lymphoid lineages. The homozygous mouse has been demonstrated to exhibit an apparent pan-hematopoiesis, resulting in the accumulation of inflammatory cells in organs and the skin and a macrophage infiltrate in the lung. The C57BL/6J 'itchy' mice have a phenotype that suggests activation of processes typical of chronic inflammatory and/or wound healing events, including lymphoid hyperplasia, hematopoietic cell proliferation and gastorintestinal epithelial hyperplasia. The mice also display chronic inflammation of airways, skin and stomach. The 'itchy' E3 ligase appears to mediate the turnover of signal transduction proteins in the hematopoietic lineages.

The murine E3 ligase (SEQ ID NO:4), involved in ubiquitin-mediated protein degradation, is believed to specifically mediate the turnover of growth factor signal transduction proteins in the hematopoietic lineages. By analogy, the human homolog E3 ubiquitin protein ligase described herein (SEQ ID NO:3) is expected to likewise significantly influence hematopoiesis. Moreover, results indicate that ubiquitin-dependent proteolysis is an important mediator of the immune response in vivo and provides evidence for the 'itchy' E3's role in inflammation and the regulation of epithelial and haematopoietic cell growth. Perry, W. L., et al., Nature Genet., 18:143 (1998); Rolfe, M., et al., *The Ubiquitin-Mediated Proteolytic Pathway as a Therapeutic Area,* J. Mol. Med. 75:5–17 (1997). Accordingly, specific modulation of the biological and/or pharmacological activity of the human "itchy" E3 ligase, e.g., SEQ ID NO:3, via administration of a compound modulator or heterologous expression or administration of a dominant negative mutant version or antisense molecule derived from SEQ ID NO:1 is expected to significantly influence inflammation as well as hematopoiesis. Modulation of the biological and/or pharmacological activity of the human 'itchy' (e.g., SEQ ID NO:3) is expected to modulate lymphocyte function, for example by inhibiting human 'itchy' activity, resulting in anti-tumor activity. Modulation of the human E3 ligase activity is moreover contemplated in applications for supportive hematopoietic therapy; for example, in subjects wherein cancer therapy impairs bone marrow function or in immune suppressed cancer patients.

Inhibition of the biological activity of 'itchy' (SEQ ID NO:3) is expected to accelerate development of the erythroid, myeloid, and lymphoid lineages. Blockage or reduction of 'itchy' (e.g., SEQ ID NO:3) activity by a compound or other pharmacologic agent is expected to stimulate hematopoiesis as well as expansion of activated lymphocytes (e.g., expand T lymphocytes in cancer patients).

Example human E3 ubiquitin protein ligase substrates include, but are not limited to, GM-CSF and its receptor, G-CSF and its receptor, SCF and its receptor c-kit, IL-3 and IL-3r, IL-5 and IL-Sr, and IL-6 and IL-6r.

Hematopoiesis can be severely compromised by cytotoxic chemotherapy and irradiation. High-dose conditioning therapies that include total body irradiation, for instance, are notably myelotoxic and require the transplantation of hematopoietic progenitor cells. See, e.g., Thomas, E. D., et al., N. Eng. J. Med., 25:491 (1987); Berenson, R. J. et al., Blood. 77:1717 (1991). Such adoptive cellular immunotherapy is regularly accompanied by growth factor administration, e.g., erythropoietin (Epogen), G-CSF (Neupogen), GM-CSF, and thrombopoietin in respective therapeutic applications. Modulators of the novel human E3 ubiquitin protein ligase as described herein are therefore contemplated as therapeutic agents to compete with the likes of erythropoietin (Epogen), G-CSF (Neupogen), and thrombopoietin in the respective applications. Applications are also contemplated for supportive hematopoietic care, including cancer therapies that impair bone marrow function and AIDS/HIV.

Cachexia is a condition characterized by severe muscle atrophy, weight loss and emaciation. Ubiquitin dependent proteolysis has been linked to the skeletal muscle loss during cachexia as well in in tumors. Medina, R., et al., Biomed.

Biochim. Acta. 50:4 (1991); Temparis, S., et al., Cancer Research, 54: 5568 (1994); Tiao, G. et al., J. Clin. Invest., 94:2255 (1994). Furthermore, ubiquitin dependent proteolysis has recently been implicated in the down regulation of signal transducing receptors. Particularly the involvement of the ubiquitin conjugation system in the ligand induced endocytosis and degradation of the growth hormone receptor may be of particular importance in cachexia conditions. The b2-Adrenergic Agonist, Clenbuterol, for instance, has been demonstrated to prevent enhanced muscle protein degradation, and that normalization of protein breakdown is achieved through a decrease of the hyperactivation of the ubiquitin dependent proteolysis system. Costelli, P., et al., J. Clin. Invest 95:2367 (1995).

The novel human E3 recombinant enzyme described herein, e.g., SEQ ID NO:3, is expected to have inherently high native catalytic activity. Clearly defined biological activity permits easy adaptation of the ligase to methods for identifying compounds that modulate the biological and/or pharmacological activity of the novel human E3 ubiquitin protein ligase and variations thereof contemplated herein, for instance, via automated high throughput biochemical assays, e.g., scintillation proximity assays, further described infra. For instance, a specific low molecular weight inhibitor of ubiquitin transfer onto cyclin B, targeting the E3 involved in this process, would prevent cyclin B destruction and would be expected to be a very strong cytostatic agent. Rolfe, M., et al., *The Ubiquitin-Mediated Proteolytic Pathway as a Therapeutic Area,* J. Mol. Med. 75:5–17 (1997). Accordingly, specific modulation of the biological and/or pharmacological activity of the novel human E3 ubiquitin protein ligase, e.g., SEQ ID NO:3, via administration of a compound modulator or heterologous expression or administration of a dominant negative mutant version is expected to have a high degree of biological specificity for the treatment of physiological conditions including, but not limited to, inflammation, autoimmune disease, neurological disease, apoptosis, endothelial cell physiology (e.g., proliferation, differentiation), peripheral vascular disease, angiogenesis, cancer, anemia, hematopoietic disorders, cachexia, leukemia, pulmonary disorders, arthritis, diabetes, and viral infection.

Variants

The present invention relates to nucleic acid (e.g., SEQ ID NO:1 and SEQ ID NO:2) and amino acid sequences (e.g., SEQ ID NO:3) of the E3 ubiquitin protein ligase, variations thereof as well as functional derivatives, and to the use of these sequences to identify compounds that modulate the biological and/or pharmacological activity of the human biomolecule. Further, the invention relates to biologically effective antisense nucleic acid molecules as well as nucleic acids which encode biologically effective dominant negative mutant versions of the E3 ubiquitin protein ligase as well as biologically effective dominant negative mutant versions of the novel peptide biomolecule. The present invention also provides a method of treatment for a patient in need of such treatment, videlicet for a patient who suffers a pathological condition mediated by the SEQ ID NO:3 E3 ubiquitin protein ligase, comprising administering an effective amount of a biologically effective antisense nucleic acid molecule derived from SEQ ID NO:1; or administering an effective amount of a nucleic acid which encodes a biologically effective dominant negative mutant version; or administering a compound that modulates a biological and/or pharmacological activity of SEQ ID NO:3 which was identified by a method described or contemplated herein.

The present invention also encompasses variants of the E3 ubiquitin protein ligase molecule, SEQ ID NO:3. A preferred variant, for instance, is a polypeptide comprising a fragment having at least 80% amino acid sequence homology (identity) to SEQ ID NO:3 and which comprises at least one amino acid, relative to the position of SEQ ID NO:3, selected from the group consisting of: V66, H70, A89, V108, G113, I122, I127, L134, S136, T145, A150, S151, S157, S159, K160, E162, D171, D175, G177, A178, R182, V184, S185, A225, T226, E228, N245, P271, T273, S380, T452, D650, and A752. A further preferred variant is a dominant negative mutant polypeptide further derived from these contemplated embodiments wherein wherein cysteine at position 820 (C820), relative to SEQ ID NO:3, is substituted or deleted.

A more preferred variant is a E3 ubiquitin protein ligase polypeptide comprising an amino acid sequence having at least about 96% homology to SEQ ID NO:3.

A most preferred variant is a E3 ubiquitin protein ligase polypeptide comprising an amino acid sequence having at least about 96% homology to SEQ ID NO:3 and comprising at least one amino acid, relative to the position of SEQ ID NO:3, selected from the group consisting of: V66, H70, A89, V108, G113, I122, I127, L134, S136, T145, A150, S151, S157, S159, K160, E162, D171, D175, G177, A178, R182, V184, S185, A225, T226. E228, N245, P271, T273, S380, T452, D650, and A752). A further preferred variant is a dominant negative mutant polypeptide further derived from these contemplated embodiments wherein wherein cysteine at position 820 (C820), relative to SEQ ID NO:3, is substituted or deleted.

A purified polynucleotide comprising a nucleic acid sequence which encodes a polypeptide of the present invention is a most preferred embodiment of the present invention.

A variant of the SEQ ID NO:3 E3 ubiquitin protein ligase of the present invention may have an amino acid sequence that is different by one or more amino acid substitutions. Embodiments which comprise amino acid deletions and/or additions are also contemplated. The variant may have conservative changes (amino acid similarity), wherein a substituted amino acid has similar structural or chemical properties, for example, the replacement of leucine with isoleucine. A variant may have nonconservative changes, e.g., replacement of a glycine with a tryptophan. Embodiments within the intended scope of the invention also include SEQ ID NO:3 having one or more amino acid deletions or insertions, or both. Guidance in determining which and how many amino acid residues may be substituted, inserted or deleted without abolishing biological or proposed pharmacological activity may be reasonably inferred in view of this disclosure and may be further be found using computer programs well known in the art, for example, DNAStar software (DNAStar Inc., Madison, Wis.).

Amino acid substitutions of SEQ ID NO:3 may be made, for instance, on the basis of similarity in polarity, charge, solubility, hydrophobicity, hydrophilicity, and/or the amphipathic nature of the residues as long as a biological and/or pharmacological activity of the native molecule is retained. However, amino acid substitutions are important to construct contemplated biologically effective dominant negative mutants, species of which are set forth herein.

Negatively charged amino acids, for example, include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine. However, in the construction of biologically effective dominant negative mutants at least one amino acid residue position at an active site required for biological and/or pharmacological activity in the native peptide is changed to produce an agent or entity having reduced activity or which is devoid of detectable native wild type activity.

Suitable substitutions of amino acids include the use of a chemically derivatized residue in place of a non-derivatized residue. D-isomers as well as other known derivatives may also be substituted for the naturally occurring amino acids. See, e.g., U.S. Pat. No. 5,652,369, Amino Acid Derivatives, issued Jul. 29, 1997. Example substitutions are set forth in TABLE 1 as follows:

TABLE 1

| Original residue | Example conservative substitutions |
| --- | --- |
| Ala (A) | Gly; Ser; Val; Leu; Ile; Pro |
| Arg (R) | Lys; His; Gln; Asn |
| Asn (N) | Gln; His; Lys; Arg |
| Asp (D) | Glu |
| Cys (C) | Ser |
| Gln (Q) | Asn |
| Glu (E) | Asp |
| Gly (G) | Ala; Pro |
| His (H) | Asn; Gln; Arg; Lys |
| Ile (I) | Leu; Val; Met; Ala; Phe |
| Leu (L) | Ile; Val; Met; Ala; Phe |
| Lys (K) | Arg; Gln; His; Asn |
| Met (M) | Leu; Tyr; Ile; Phe |
| Phe (F) | Met; Leu; Tyr; Val; Ile; Ala |
| Pro (P) | Ala; Gly |
| Ser (S) | Thr |
| Thr (T) | Ser |
| Trp (W) | Tyr; Phe |
| Tyr (Y) | Trp; Phe; Thr; Ser |
| Val (V) | Ile; Leu; Met; Phe; Ala |

"Homology" is a measure of the identity of nucleotide sequences or amino acid sequences. In order to characterize the homology, subject sequences are aligned so that the highest order homology (match) is obtained. "Identity" per se has an art-recognized meaning and can be calculated using published techniques. Computer program methods to determine identity between two sequences, for example, include DNAStar software (DNAStar Inc., Madison, Wis.); the GCG program package (Devereux, J., et al., Nucleic Acids Research (1984) 12(1):387); BLASTP, BLASTN, FASTA (Atschul, S. F. et al., J Molec Biol (1990) 215:403). Homology (identity) as defined herein is determined conventionally using the well known computer program, BEST-FIT (Wisconsin Sequence Analysis Package, Version 8 for Unix, Genetics Computer Group, University Research Park, 575 Science Drive, Madison, Wis. 53711). When using BESTFIT or any other sequence alignment program to determine whether a particular sequence is, for example, about 80%, or about 96% homologous to a reference sequence. According to the present invention, the parameters are set such that the percentage of identity is calculated over the full length of the reference amino acid sequence and that gaps in homology of up to, for example, about 20% or 4% of the total number of positions in the reference sequence are allowed. Eighty percent or ninety six percent of homology is therefore determined, for example, using the BESTFIT program with parameters set such that the percentage of identity is calculated over the full length of the reference sequence, e.g., SEQ ID NO:3, and gaps of up to 20% or 4%, respectively, of the total number of amino acids in the reference sequence are allowed, and wherein up to 20% or 4% of the amino acid residues in the reference sequence may be deleted or substituted with another amino acid, or a number of amino acids up to 20% or 4% of the total amino acid residues in the reference sequence may be inserted into the reference sequence. Percent homologies are likewise determined, for example, to identify preferred species, within the scope of the claims appended hereto, which reside within the range of about 80 percent to 100 percent homology to SEQ ID NO:3 as well as biologically and/or pharmacologically active functional derivatives thereof and biologically effective dominant negative mutants contemplated herein.

Percentage similarity (conservative substitutions) between two polypeptides may also be scored by comparing the amino acid sequences of the two polypeptides by using programs well known in the art, including the BESTFIT program, by employing default settings for determining similarity.

Polynucleotide sequences which encode the E3 ubiquitin protein ligase as depicted in SEQ ID NO:3 and variants thereof contemplated herein are particularly preferred embodiment of the present invention. Biologically effective antisense molecules and nucleic acids which encode biologically effective dominant negative mutant versions of SEQ ID NO:3, or derivatives thereof, as well as dominant negative mutant versions of SEQ ID NO:3, and derivatives thereof, examples of each of which are described infra, are preferred embodiments of the present invention and are intended to fall within the scope of the claims appended hereto.

The invention also relates to pharmaceutical compounds and compositions comprising the molecule substantially as depicted in SEQ ID NO:2, or variations thereof contemplated herein, or antisense molecules capable of disrupting expression of the naturally occurring gene. These compositions are useful for the prevention or treatment of conditions mediated by the E3 ubiquitin protein ligase molecule.

Dominant/negative mutants are also contemplated wherein codons for one or more known functional residues are deleted or changed in the coding region (e.g., SEQ ID NO:2) in order to encode a mutant variation having valuable pharmacological function. For example, characteristic residues for ubiquitin transfer (e.g., the conserved cysteine residue at SEQ ID NO:3 position 820 where a ubiquitin linkage is expected to occur) may be changed or deleted. See, Example VIII. Methods of treatment of conditions manifested by aberrant forms and/or abnormal levels of the native E3 ubiquitin protein ligase via administration of a nucleic acid comprising the sequence substantially as depicted in SEQ ID NO:2, as referred to herein, is defined to encompass dominant/negative mutant versions of these entities.

The human E3 ubiquitin protein ligase biomolecules of the present invention can also be used in screening assays to identify blockers, antagonists or inhibitors which bind, emulate substrate, or otherwise inactivate or compete with the biomolecule. The novel E3 ubiquitin protein ligase can also be used in screening assays to identify agonists which activate the E3 ubiquitin ligase or otherwise induce the production of or prolong the lifespan of the biomolecule in vivo or in vitro.

PCR primers, SEQ ID NO:5 and SEQ ID NO:6, are disclosed which are used to amplify the 2559 bp coding region (SEQ ID NO:2) of the novel human E3 ubiquitin protein ligase from human tissue.

Generally Acceptable Vectors

In accordance with the present invention, polynucleotide sequences which encode the human E3 ubiquitin protein ligase polypeptide, fragments of the polypeptide, fusion proteins, or functional equivalents thereof may be used in recombinant DNA molecules that direct the expression of the ubiquitin ligase biomolecule in appropriate host cells. Due to the inherent degeneracy of the genetic code, other DNA sequences which encode substantially the same or a functionally equivalent amino acid sequence, may be used to clone and express the human biomolecule as well as variations thereof contemplated herein. As will be understood by those of skill in the art, it may be advantageous to produce the human E3 ubiquitin ligase encoding nucleotide sequences which possess non-naturally occurring codons.

Specific initiation signals may also be required for efficient translation of an E3 ubiquitin ligase nucleic acid sequence. These signals include the ATG initiation codon and adjacent sequences. In cases where the human E3 ubiquitin ligase nucleic acid sequence, e.g., SEQ ID NO:2, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic.

Nucleic acid sequences, e.g., SEQ ID NO:2, may be recombinantly expressed to produce a pharmacologically active E3 ubiquitin ligase biomolecule by molecular cloning into an expression vector containing a suitable promoter and other appropriate transcription regulatory elements, and transferred into prokaryotic or eukaryotic host cells to produce the novel polypeptide. Techniques for such manipulations are, for instance, fully described in Sambrook, J., et al., Molecular Cloning Second Edition, Cold Spring Harbor Press (1990), and are well known in the art.

Express ion vectors are described herein as DNA sequences for the transcription of cloned copies of genes and the translation of their mRNAs in an appropriate host cell. Such vectors can be used to express nucleic acid sequences in a variety of hosts such as bacteria, bluegreen algae, plant cells, insect cells, fungal cells, human, and animal cells. Specifically designed vectors allow the shuttling of DNA between hosts such as bacteria-yeast, or bacteria-animal cells, or bacteria-fungal cells, or bacteria-invertebrate cells.

A variety of mammalian expression vectors may be used to express the recombinant E3 ubiquitin ligase molecule and variations thereof disclosed herein in mammalian cells. Commercially available mammalian expression vectors which are suitable for recombinant expression, include but are not limited to, pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565), pLXIN and pSIR (CLONTECH), pIRES-EGFP (CLONTECH). INVITROGEN corporation provides a wide variety of commercially available mammalian expression vector/systems which can be effectively used with the present invention. INVITROGEN, Carlsbad, Calif. See, also, PHARMINGEN products, vectors and systems, San Diego, Calif.

Baculoviral expression systems may also be used with the present invention to produce high yields of biologically active protein. Vectors such as the CLONETECH, BacPak™ Baculovirus expression system and protocols are preferred which are commercially available. CLONTECH, Palo Alto, Calif. Miller, L. K., et al., Curr. Op. Genet. Dev. 3:97 (1993); O'Reilly, D. R., et al., *Baculovirus Expression Vectors: A Laboratory Manual,* 127. Vectors such as the INVITROGEN, MaxBac™ Baculovirus expression system, insect cells, and protocols are also preferred which are commercially available. INVITROGEN, Carlsbad, Calif.

Example Host Cells

Host cells transformed with a nucleotide sequence which encodes a E3 ubiquitin ligase molecule of the present invention may be cultured under conditions suitable for the expression and recovery of the encoded protein from cell culture. Particularly preferred embodiments of the present invention are host cells transformed with a purified polynucleotide comprising a nucleic acid sequence encoding the polypeptide having the sequence substantially as depicted in SEQ ID NO:3 or a biologically active fragment thereof. Cells of this type or preparations made from them may be used to screen for pharmacologically active modulators of the activity of the human E3 ubiquitin ligase. Modulators thus identified will be used for the treatment of disorders manifested by berrant forms and/or abnormal levels of the native E3 ubiquitin protein ligase.

Eukaryotic recombinant host cells are especially preferred as otherwise described herein or are well known to those skilled in the art. Examples include but are not limited to yeast, mammalian cells including but not limited to cell lines of human, bovine, porcine, monkey and rodent origin, and insect cells including but not limited to Drosophila and silkworm derived cell lines. Cell lines derived from mammalian species which may be suitable and which are commercially available, include but are not limited to, L cells L-M(TK-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616),BS-C-1 (ATCC CCL 26) and MRC-5 (ATCC CCL 171).

The expression vector may be introduced into host cells expressing the ubiquitin ligase polypeptide via any one of a number of techniques including but not limited to transformation, transfection, lipofection, protoplast fusion, and electroporation. Commercially available kits applicable for use with the present invention for hererologous expression, including well-characterized vectors, transfection reagents and conditions, and cell culture materials are well-established and readily available. CLONTECH, Palo Alto, Calif.; INVITROGEN, Carlsbad, Calif.; PHARMINGEN, San Diego, Calif.; STRATAGENE, LaJolla, Calif. The expression vector-containing cells are clonally propagated and individually analyzed to determine the level of the novel E3 ubiquitin protein ligase production. Identification of host cell clones which express the polypeptide may be performed by several means, including but not limited to immunological reactivity with antibodies described herein, and/or the presence of host cell-associated specific E3 ubiquitin protein ligase activity, and/or the ability to covalently cross-link specific substrate to the E3 ubiquitin protein ligase polypeptide with the bifunctional cross-linking reagent disuccinimidyl suberate or similar cross-linking reagents.

The ubiquitin protein ligase biomolecule of the present invention may also be expressed as a recombinant protein with one or more additional polypeptide domains added to facilitate protein purification. Such purification facilitating domains include, but are not limited to, metal chelating peptides such as histidine-tryptophan modules that allow purification on immobilimmobilized metals (Porath, J., Protein Exp. Purif., 3:263 (1992)), protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and the ubiquitin protein ligase coding region is useful to facilitate purification.

Systems such as the CLONTECH, TALON™ nondenaturing protein purification kit for purifying 6xHis-tagged proteins under native conditions and protocols are preferred which are commercially available. CLONTECH, Palo Alto, Calif.

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a nascent form of the protein may also be important for correct insertion, folding and/or function. Different host cells such as CHO, HeLa, MDCK, 293, WI38, NIH-3T3, HEK293 etc., have specific cellular machinery and characteristic mechanisms for such post-translational activities and may be chosen to ensure the correct modification and processing of the introduced, foreign protein.

For long-term, high-yield production of the recombinant molecule, stable expression is preferred. For example, cell lines which stably express the novel E3 ubiquitin protein ligase polypeptide may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

The human E3 ubiquitin protein ligase and variations thereof described herein can be produced in the yeast S.cerevisiae following the insertion of the optimal cDNA cistron into expression vectors designed to direct the intracellular or extracellular expression of the heterologous protein. In the case of intracellular expression, vectors such as EmBLyex4 or the like are ligated to the beta subunit cistron. See, e.g., Rinas, U., et al., Biotechnology, 8:543 (1990); Horowitz, B., et al., J. Biol. Chem., 265:4189 (1989). For extracellular expression, a ubiquitin protein ligase coding region, e.g., SEQ ID NO:2, is ligated into yeast expression vectors which may employ any of a series of well-characterized secretion signals. Levels of the expressed ubiquitin ligase molecule may be determined, for example, by means of the assays described herein.

A variety of protocols for detecting and measuring the expression of the human E3 ubiquitin protein ligase, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes may be employed. Well known competitive binding techniques may also be employed. See, e.g., Hampton, R., et al. (1990), Serological Methods—aLaboratory Manual, APS Press, St Paul Minn.; Maddox, D. E., et al., J. Exp. Med. 158:1211.

Example Transformations

E coli transformations are generally carried out via electroporation. 400 ml cultures of strains DH5a or BL2 1 (DE3) are grown in L-broth to an OD 600 of 0.5 and harvested at 2,000 g. The cells are washed twice in ice-cold deionised water, resuspended in 1 ml 10% glycerol and stored in aliquots at −70° C. Ligation mixes are desalted using millipore V series membranes (0.0025 mm pore). 40 ml of cells are incubated with lull of ligation mix or plasmid DNA on ice for 10 minutes in 0.2 cm electroporation cuvettes, then pulsed using a Gene Pulser apparatus (BioRad) at ^0.5 k $Vcm^{-1}$, 25 mF, 250½. Transformants are selected on L-agar supplimented with tertracyline at 10 mg/ml or ampicillian at 100 mg/ml.

Example Expression/Puririication

The novel human E3 ubiquitin protein ligase, e.g., SEQ ID NO:2, is expressed from a pET vector (e.g., 14b–16b or 28a–c(+) (NOVAGEN)) in BL21 cells, in such a way to produce a recombinant protein containing a 6-histidine tag immediately adjacent to the N-tenninal methionine. The 6-His tag is used to aid purification of the recombinant protein as is passed through a nickel chelating column (NOVAGEN).

Over-Expression of the Ubiquitin Ligase in Cell-Lines

Transient and/or stable eucaryotic transfectant cells comprised of the coding region(s) described herein are contemplated for high-level expression of the novel human E3 ubiquitin protein ligase as well as variations thereof.

Eucaryotic transfectants are preferred embodiments of the present invention for employment in studies for the identification molecules which modulate the human E3 ubiquitin protein ligase described herein in vivo. HEK cells, for example, may be employed.

Transient expression of coding regions for the human E3 ubiquitin protein ligase polypeptide can be achieved by straight transfection into mammalian cells, by standard techniques. Omari, K. et al., J. Physiol., 499:369, (1997); Panyi, G. et al., J. Gen. Physiol., 107(3):409 (1996). High level transient expression may be achieved using standard viral systems, e.g., Baculovirus, Adenovirus, or Vaccinia virus. Functionally expressed representatives resulting from these systems are typically 5–500K per cell. Kamb, A., Methods Enzymol. 207:423 (1992); Sun, T. et al., Biochemistry, 33(33):9992 (1994); Spencer, R. H., et al., J. Biol. Chem., 272:2389 (1997).

Stable transfection of heterologous cells using sequences which encode the novel E3 ubiquitin protein ligase described herein (SEQ ID NO:3) or pharmacologically active variations or fragments thereof can be generated using, for example, NIH-3t3, L929, COS, HEK, or CHO cells. See, e.g., EMBO, 11 (6):2033 (1992); Grissmer, et al., Mol. Pharm., 45:1227 (1994).

A preferred vector for use with the present invention is pcDNA/Neo, which is commercially available from INVITROGEN, Carlsbad, Calif.

Cells, NIH-3t3, for example, are grown to 50% confluency in 60 mm plates (media and conditions are according to requirements of the particular cell line) and transfected with 5 ug of pure DNA comprising a coding region for the human E3 ubiquitin protein ligase, e.g. SEQ ID NO:2, in pCDNA/Neo using the Lipofection reagent, as described by the supplier (LIFE TECHNOLOGIES Gibco BRL, Bethesda, Md.). After transfection, the cells are incubated at 37° C., conditions for 3 days in medium with 10% FCS. Cells are trypsinized seeded onto 100 mm dishes, and then selected with 300 ug/ml of G418 (Neomycin). Only cells that have stable integration of the heterologous coding region will grow in the presence of G418, which is conferred by the Neomycin-resistance gene in the plasmid. Isolated clones are processed for 2–3 rounds of purification.

Example Generation of Human 'Itchy' Constructs

Human kidney cDNA was subjected to PCR using the following primers to isolate the full-length coding region of the human itchy E3 ligase (SEQ ID NO:3): upper: 5'-GTCTGACAGTGGATCACAAC-3' (SEQ ID NO:12); lower: 5'-CCATTCATGGTGCAAGTTCTC-3' (SEQ ID NO:13). PCR conditions were 94° C. 3 minutes; 31 cycles of 94° C. 1 minute, 58° C. 1 minute, 72° C. 2 minutes 30 seconds 72° C. 3 minutes. The resulting 2616 bp product was cloned into the pCR2.1 TOPO TA cloning vector (Invitrogen, Carlsbad, Calif.) according to manufacturer's instructions except transformations were performed in ME DH5α cells. An N-terminal glutathione-S-transferase (GST)-itchy fusion construct was made by digesting the wild-type itchy TOPO vector with Eco RV and Spe I and cloning the purified insert into a Sma I-cut pGEX-5x-3 vector (Pharmacia, Piscataway, N.J.) by blunt-end ligation (E3/pGEX-5x-3). An N-terminal green fluorescent protein (GFP) fusion construct for expression in mammalian cells was made by digesting the wild-type GST fusion construct with Bam HI and Not I and ligating the purified insert into the same sites in the pEGFP-C1 vector E3/pEGFP-C1 (Clontech, Palo Alto, Calif.). *Expression of gst fusion constructs*; see Example VI. Each of the anti-SEQ ID NO:3 peptide antibodies described herein (infra) were demonstrated via western blot to react strongly with the SEQ ID NO:3 fusion product.

E1

All ubiquitin-activating (E1) proteins and genes corresponding thereto are contemplated for use in biological assays as well as drug screen assays described herein. SEQ ID NO:10, for example, as an embodiment for use in the methods described and contemplated herein, is the 3177 base translated structural coding region of the nucleic acid sequence which encodes the previously described 1058 amino acid residue human E1 ubiquitin activating enzyme (Uba1). Ayusawa, D., etal., Cell Struct. Funct., 17:113 (1992). See, also, Jentsch, S., et al., *Genetic Analysis of the Ubiquitin System*, Biochim. Biophys. Acta, 1089:127 (1991); McGrath, J.P., et al., *UBA1—An Essential Yeast Gene Encoding Ubiquitin-Activating Enzyme*, EMBO 10: 227 (1991); *Immunofluorescent Localization of the Ubiquitin-Activating Enzyme, E1, to the Nucleus and Cytoskeleton*, Am. J. Physiol, 264:C9; Cook, J. C., et al., *Ubiquitin-Activating Enzyme in Cultured Cells*, PNAS, 92:3454 (1995); Nagai, Y., et al., *Ubiquitin-Activating Enzyme, E1, is Phosphorylated in Mammalian Cells by the Protein Kinase Cdc2*, J. Cell Sci., 108:2145 (1995).

E2

Similarly, all ubiquitin-conjugating enzymes (E2) proteins and genes corresponding thereto are contemplated for use in biological assays as well as drug screen assays described herein. SEQ ID NO: 11, for example, as an embodiment for use in the methods described and contemplated herein, is the 444 base translated structural coding region of the nucleic acid sequence which encodes the previously described 147 amino acid residue E2 ubiquitin conjugating enzyme E217k (ub10a). Wing S. S., et al., Biochem. J., 305:125 (1995) [The E2 human version (Ubc2) is preferred as described by Koken, M., et al., PNAS, 88:8865 (1991)]. Other embodiments of E2 ubiquitin conjugating enzymes for use in methods of the present invention include, but are not limited to: Ubc2/Rad6 (Koken, M., et al., PNAS, 88:8865 (1991) *Human E2*), Ubc3/Cdc34 (Plon, et al., PNAS, 90:10484 (1993)), Ubc4/Ubc5B (Jensen, et al., J. Biol. Chem., 270:30408 (1995) & Rolfe, et al., PNAS, 92:3264 (1995)), Ubc5/Ubc5A (Jensen, et al., J. Biol. Chem., 270:30408 (1995) & Schneffer, et al., PNAS, 91:8797 (1994)), Ubc5C (Jensen, et al., J. Biol. Chem., 270:30408 (1995)), Ubc6 (Nuber, et al., J Biol Chem 271:2795 (1996)), Ubc7 (Nuber, et al., J Biol Chem 271:2795 (1996) & Robinson, et al., Mammal Genome, 6:725 (1995)), Ubc8 (Kaiser, et al., J Biol Chem, 269:8797 (1994)), Ubc9 (Kovalenko, et al., PNAS, 93:2958 (1996)), Watanabe, et al., Cytogen Cell Gen ., 72:86 (1996), Ubc-epi (Liu, et al., *cDNA Cloning of a Novel Human Ubiquitin Carrier Protein*, J. Biol. Chem., 267:15829 (1992)), and Ubc-bendless: GENBANK Accession Number D83004. See, *generally*, Rolfe, et al., *The Ubiquitin-Mediated Proteolytic Pathway as a Therapeutic Area, J. Mol. Med.*, 75:5 (1997)). See, also, Baboshina, O.V., et al., *Novel Multiubiquitin Chain Linkages Catalysed by the Conjugating Enzymes E2(EPF) and RAD6 are recognized by the 26-S Proteasome Subunit*, J. Biol Chem., 271:2823 (1996); Dohmen, R. J., et al., *The N-End Rule Is Mediated by the Ubc2(Rad6) Ubiquitin-Conjugating Enzyme*, PNAS, 88:7351 (1991); Seufert, W., et al., *Ubiquitin-Conjugating Enzymes Ubc4 and Ubc5 Mediate Selective Degradation of Short-Lived and Abnormal Proteins*, EMBO, 9:543 (1990); Cook, W. J., et al., *3-Dimensional Structure of a Ubiquitin-Conjugating Enzyme* (E2), J. Biol. Chem., 267:15116 (1992); Bartel, B., et al., *The Recognition Component of the N-End Rule Pathway*, EMBO, 9:3179 (1990).

Ubiquitin

Ubiquitin is available, labeled and unlabeled, from a variety of well-known commercial suppliers. SEQ ID NO:7 is the 156 amino acid precursor peptide to the mature 76 amino acid residue sequence of human ubiquitin (Lund P. K., et al., J. Biol. Chem., 260:7609 (1985)). SEQ ID NO:8 is the mature 76 amino acid residue sequence of native human ubiquitin (positions 1–76 of SEQ ID NO:7). SEQ ID NO:9 is the 471 base translated structural coding region of the cDNA nucleic acid sequence which encodes the 156 amino acid precursor peptide (SEQ ID NO:7) to the mature 76 amino acid residue sequence of native human ubiquitin (positions 1–76 of SEQ ID NO:7) (Lund P. K., et al., J. Biol. Chem., 260:7609 (1985)). The human E3 ubiquitin protein ligase (SEQ ID NO:3) ubiquitinates specific intracellular biological molecules in vivo including the likes of intracellular messenger biological molecules, receptors, ligands, signal transduction molecules, transcriptional activators, cytokines, kinases, and phosphorylases, especially which mediate physiological conditions such as inflammation, autoimmune disease, neurological disease, apoptosis, endothelial cell physiology (e.g., proliferation, differentiation), peripheral vascular disease, angiogenesis, cancer, anemia, hematopoietic disorders, cachexia, leukemia, pulmonary disorders, arthritis, diabetes, and viral infection to effect selective destruction and swift regulation of cellular physiology. Any potential substrate may be used in biological assays as well as drug screen assays described herein including, but not limited to, substrates referred to in references cited herein or which are otherwise known or identified in the art of human pathophysiology.

General Assays

Methods of identifying compounds that modulate a biological and/or pharmacological activity of a E3 ubiquitin protein ligase, are contemplated and provided herein and in the EXAMPLES which comprise combining a candidate compound modulator of E3 ubiquitin protein ligase biological and/or pharmacological activity with a human E3 ubiquitin protein ligase polypeptide having the sequence substantially as depicted in SEQ ID NO:3, and measuring an effect of the candidate compound modulator on the biological and/or pharmacological activity.

The human E3 ubiquitin protein ligase described herein may be assayed for its ability to modulate protein degradation or selective proteolysis and/or otherwise modulate conditions associated with aberrant ubiquitin dependent proteolysis in intracellular physiology (disorders manifested by aberrant forms and/or abnormal levels of the native E3 ubiquitin protein ligase). Methods of identifying compounds that modulate the pharmacological activity of a E3 ubiquitin protein ligase, comprise combining a candidate compound modulator of E3 ubiquitin protein ligase pharmacological activity with a host-cell expressing a E3 ubiquitin protein ligase polypeptide having the sequence substantially as depicted in SEQ ID NO:3, and measuring an effect of the candidate compound modulator on the pharmacological activity.

Scintillation Proximity Assay

Scintillation Proximity Assay (SPA) technology is developed which allows the rapid and sensitive assay of a wide variety of molecular interactions in a homogeneous system. AMERSHAM, Bucks, UK. The decay of a radioactive atom releases sub-atomic particle radiation. The distance these particles travel through the medium in which they are released is dependent upon the energy of the particle. In the scintillation proximity assay scintillant is incorporated into small fluoromicrospheres. These microspheres or 'beads' are derivatized in such a way as to bind specific molecules. If a radioactive molecule is bound to the bead, the radiation is in close enough proximity to stimulate the scintillant in order to emit light (unbound isotopes are too distant). The technique of SPA simplifies the process of assay design by removing the necessity to separate bound from free ligand, allowing assays to be performed and counted in one tube or in 96-well microplates. Moreover, assay speed is increased, and the need for filters, solvents, vials and scintillation reagents is eliminated. SPA is employed in screening assays as diverse as protein:protein, protein:DNA and cell adhesion molecule interactions. SPA represents a major drug screening technology, which has already been used successfully to identify a large number of candidate therapeutic compounds against a multitude of targets. See, EXAMPLE III.

FIG. 1 shows a schematic representation of example Scintillation Proximity Assays (SPA), as well as RIA and ELISA Assays.

Human E3 ubiquitin protein ligase may be therefore assayed for inherent pharmacological properties which may be useful to exploit for therapeutic purposes, i.e., administration via gene therapy or otherwise, in vivo, to control the selective elimination of intracellular biomolecules and hence regulate physiology.

Ubiquination Assays

Ubiquination reactions were performed using a protocol based on that used by Hatakeyama, et al. J. Biol. Chem., 272:15085 (1997). See, Example VII; FIG. 2.

The assay may be made quantitative by comparing the expression or function of a test sample with the levels of expression or function in a standard sample.

The E3 ubiquitin protein ligase described herein, its immunogenic fragments or oligopeptides can be used for screening therapeutic compounds in any of a variety of drug screening techniques. The fragment employed in such a test may be free in solution, affixed to a solid support, borne on a cell surface, or located intracellularly. The abolition of activity or the formation of binding complexes, between the E3 ubiquitin ligase biomolecule and the agent being tested, may be measured. Accordingly, the present invention provides a method for screening a plurality of compounds for specific binding affinity with the E3 ubiquitin protein ligase polypeptide or a fragment thereof, comprising providing a plurality of compounds; combining a polypeptide of the present invention or a fragment thereof with each of a plurality of compounds for a time sufficient to allow binding under suitable conditions; and detecting binding of the subunit, or fragment thereof, to each of the plurality of compounds, thereby identifying the compounds which specifically bind the E3 ubiquitin protein ligase. Compounds that modulate the biological activity of E3 ubiquitin protein ligase identified in this manner are especially preferred embodiments of the invention.

A further embodiment of the present invention is a method of modulating a biological and/or pharmacological activity of a E3 ubiquitin protein ligase polypeptide in a cell comprising administering an effective amount of a polynucleotide of the present invention to said cell.

A further embodiment of the present invention is a method of modulating a biological and/or pharmacological activity of a E3 ubiquitin protein ligase polypeptide in a cell comprising administering an effective amount of a compound identified by means of a method described herein to said cell.

Compounds and Methods

Compounds which are identified generally according to methods described, referenced, and contemplated herein that modulate the biological and/or pharmacological activity of E3 ubiquitin protein ligase are especially preferred embodiments of the present invention. Therefore, as an inherent corollary, a method of the present invention is the treatment of a patient in need of such treatment for a condition which is mediated by the biological and/or pharmacological activity of a human E3 ubiquitin protein ligase, comprising administration of a compound that modulates the biological and/or pharmacological activity of a human E3 ubiquitin protein ligase identified by a method described herein.

A further method of the present invention is treatment of a patient in need of such treatment for a condition which is mediated by the biological and/or pharmacological activity of a human E3 ubiquitin protein ligase, comprising administration of the E3 ubiquitin protein ligase substantially as depicted in SEQ ID NO:3 or a variant contemplated herein. Therapeutic methods of the present invention also include treatment of a patient in need of such treatment for a condition which is mediated by the biological and/or pharmacological activity of a human E3 ubiquitin protein ligase, comprising administration of a nucleic acid which comprises the sequence substantially as depicted in SEQ ID NO:2 or variant contemplated herein. Therapeutic methods of the present invention furthermore include treatment of a patient in need of such treatment for a condition which is mediated by the biological activity of a human E3 ubiquitin protein ligase, comprising administration of an antisense molecule comprising the complement of the sequence substantially as depicted in SEQ ID NO:2 or a biologically-effective fragment thereof (further discussed infra).

Example Dominant Negative Mutant

Figure 3:
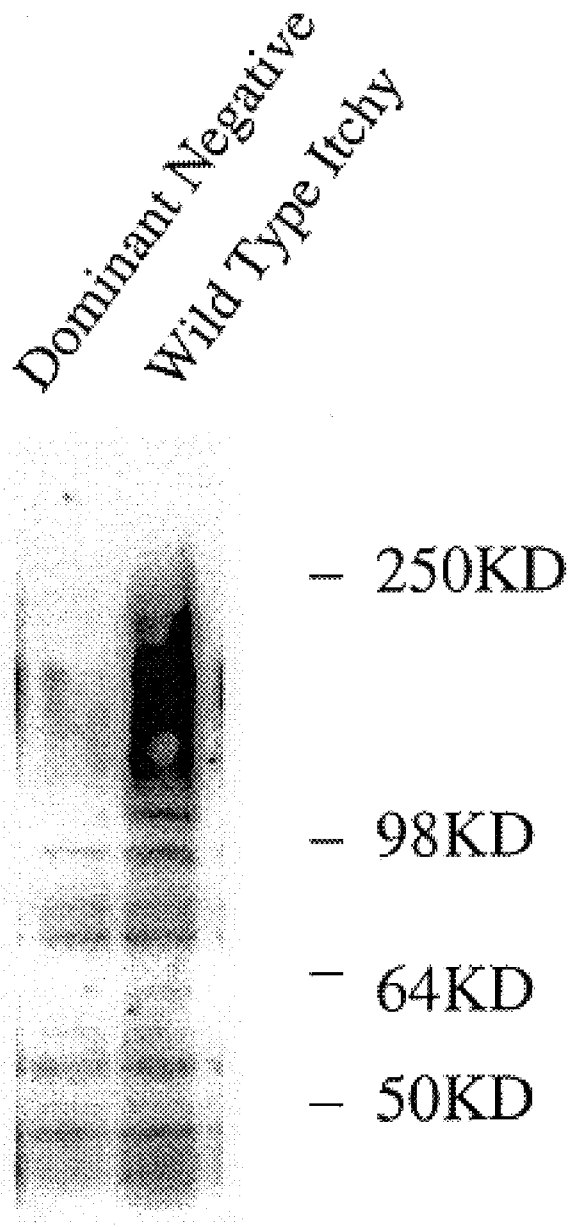
FIG. 3 demonstrates the dominant negative construct (C820A) has no enzymatic activity (ubiquitination) compared to the wild type control.

To prove that the active site cysteine in the human itchy gene is essential for ubiquitination, bbacterially expressed protein from the dominant negative construct (C820A, described herein) was used in ubiquitination assays. The results (Example VIII; FIG. 3) demonstrate that the dominant negative construct (C820A) has no enzymatic activity (ubiquitination) compared to the wild type control. See Example VIII; FIG. 3. Ubiquitination substrate (DH5a bacterial Lysates). 12% SDS-PAGE. Primary Ab (anti-ubiquitin) -Secondary Ab (Anti-rabbit Ig). Western blot developed using ECL system (Amersham, Bucks, UK).

Antisense Molecules

To enable methods of down-regulating expression of the human E3 ubiquitin protein ligase1 of the present invention in mammalian cells, an example antisense expression construct containing the complement DNA sequence to the sequence substantially as depicted in SEQ ID NO:2 can be readily constructed for instance using the pREP 10 vector (Invitrogen Corporation). Transcripts are expected to inhibit translation of the wild-type E3 ubiquitin protein ligase mRNA in cells transfected with this type construct. Antisense transcripts are effective for inhibiting translation of the native gene transcript, and capable of inducing the effects (e.g., regulation of physiological disorders) herein described. Translation is most effectively inhibited by blocking the mRNA at a site at or near the initiation codon. Thus, oligonucleotides complementary to the corresponding 5'-terminal region of the human E3 ubiquitin protein ligase mRNA transcript (SEQ ID NO:2) are preferred. Secondary or tertiary structure which might interfere with hybridization is minimal in this region. Moreover, sequences that are too distant in the 3' direction from the initiation site can be less effective in hybridizing the mRNA transcripts because of a "read-through" phenomenon whereby the ribosome appears to unravel the antisense/sense duplex to permit translation of the message. Oligonucleotides which are complementary to and hybridizable with any portion of the human E3 ubiquitin protein ligase mRNA are contemplated for therapeutic use.

U.S. Pat. No. 5,639,595, Identification of Novel Drugs and Reagents, issued Jun. 17, 1997, wherein methods of identifying oligonucleotide sequences that display in vivo activity are thoroughly described, is herein incorporated by reference. Expression vectors containing random oligonucleotide sequences derived from previously known polynucleotides, e.g., SEQ ID NO:1, are transformed into cells. The cells are then assayed for a phenotype resulting from the desired activity of the oligonucleotide. Once cells with the desired phenotype have been identified, the sequence of the oligonucleotide having the desired activity can be identified. Identification may be accomplished by recovering the vector or by polymerase chain reaction (PCR) amplification and sequencing the region containing the inserted nucleic acid material.

An antisense molecule derived from and complementary to SEQ ID NO:1 is a particularly preferred embodiment of the present invention. The complement of SEQ ID NO:2 is a preferred species. Antisense molecules which comprise oligomers in the range from about 12 to about 25 nucleotides which are complementary to regions of SEQ ID NO:1 and/or SEQ ID NO:2 are preferred embodiments of the invention. Antisense molecules comprising oligomers from about 12 to about 25 nucleotides in length which are complementary to a region within 65 nucleotides of the start codon or the stop codon of SEQ ID NO:1 are preferred.

Nucleotide sequences that are complementary to the novel E3 ubiquitin protein ligase polypeptide encoding polynucleotide sequence can be synthesized for antisense therapy. These antisense molecules may be DNA, stable derivatives of DNA such as phosphorothioates or methylphosphonates, RNA, stable derivatives of RNA such as 2'-O-alkylRNA, or other oligonucleotide mimetics. U.S. Pat. No. 5,652,355, Hybrid Oligonucleotide Phosphorothioates, issued Jul. 29, 1997, and U.S. Pat. No. 5,652,356, Inverted Chimeric and Hybrid Oligonucleotides, issued Jul. 29, 1997, which describe the synthesis and effect of physiologically-stable antisense molecules, are incorporated by reference. Human E3 ubiquitin protein ligase antisense molecules may be introduced into cells by microinjection, liposome encapsulation or by expression from vectors harboring the antisense sequence. Antisense therapy may be particularly useful for the treatment of diseases where it is beneficial to modulate the biological activity and/or pharmacological activity of the human E3 ubiquitin protein ligase described herein.

Gene Therapy

The human E3 ubiquitin protein ligase polypeptide and variations thereof contemplated herein may administered to a subject via gene therapy. A polypeptide of the present invention may be delivered to the cells of target organs, e.g., hematopoietic cells, in this manner. Conversely, human E3 ubiquitin protein ligase polypeptide antisense gene therapy may be used to modulate the expression of the polypeptide in the same cells of target organs and hence regulate biological and/or pharmacological activity. The human E3 ubiquitin protein ligase coding region can be ligated into viral vectors which mediate transfer of the trans-activator polypeptide nucleic acid by infection of recipient host cells. Suitable viral vectors include retrovirus, adenovirus, adeno-associated virus, herpes virus, vaccinia virus, polio virus and the like. See, e.g., U.S. Pat. No. 5,624,820, Episomal Expression Vector for Human Gene Therapy, issued Apr. 29, 1997.

Nucleic acid coding regions of the present invention are incorporated into effective eukaryotic expression vectors, which are directly administered or introduced into somatic cells for gene therapy (a nucleic acid fragment comprising a coding region, preferably mRNA transcripts, may also be administered directly or introduced into somatic cells). See, e.g., U.S. Pat. No. 5,589,466, issued Dec. 31, 1996. Such nucleic acids and vectors may remain episomal or may be incorporated into the host chromosomal DNA as a provirus or portion thereof that includes the gene fusion and appropriate eukaryotic transcription and translation signals, i.e, an effectively positioned RNA polymerase promoter 5' to the transcriptional start site and ATG translation initiation codon of the gene fusion as well as termination codon(s) and transcript polyadenylation signals effectively positioned 3' to the coding region. Alternatively, the human E3 ubiquitin protein ligase DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo, as well as in vivo human gene therapy according to established methods in this art.

EXAMPLES

Example I

A. Ubiquitin Thioester Conjugation Assay for Biological Activity

Ubiquitin thiol ester formation by the novel human E3 ubiquitin protein ligase (e.g., SEQ ID NO:3) is determined by change in SDS-PAGE mobility of the E3 ligase band (characteristic of thioester formation between ubiquitin and the protein in this gel-shift assay). Reaction mixtures contain 5–10 ng of recombinant E1 (SEQ ID NO:10) which is the translated structural coding region of human E1 ubiquitin activating enzyme Uba1), 100 ng of recombinant E2 (SEQ ID NO:11) which is the translated structural coding region of the E2 ubiquitin conjugating enzyme E217k) [The human version (Ubc2) is preferred as described by Koken, M., et al., PNAS, 88:8865 (1991)], 200 ng of $^{32}$P-labeled human E3 ligase (SEQ ID NO:3), and 500 ng of GST-ubiquitin in 20 mM Tris-HCl, pH 7.6, 50 mM NaCl, 4 mM ATP, 10 mM MgC12, and 0.2 mM dithiothreitol for 3 min at 25 ° C. Human E3 ubiquitin protein ligase reactions are terminated by incubating the mixtures for 15 min at 30 ° C. in SDS-sample buffer (50 mM Tris-HCl, pH 6.8, 2% SDS, 10% glycerol, and 0.2% bromphenol blue) in the absence of reducing agents and resolved by SDS-PAGE. Radioactively labeled proteins are visualized by autoradiography. Change in the mobility of the E3 ligase band indicates thioester formation in this gel-shift assay. See, *alternate techniques*, e.g., Huibregtse, J. M., et al., *The HPV-16 E6 and E6-AP Complex Functions as a Ubiquitin-Protein Ligase in the Ubiquitination of p53*, Cell, 75:495 (1995).

Example II
Ubiquitination Assay for Biological Activity

Physical interaction between specific E2 enzymes (for example, E2 17k (SEQ ID NO:11 (structural coding region))) [The human version (Ubc2) is preferred as described by Koken, M., et al., PNAS, 88:8865 (1991)] and the novel human E3 ubiquitin protein ligase (e.g., SEQ ID NO:3) characterizes specific functional cooperativity. This assay employs [$^{35}$S]Methionine-labeled proteins synthesized in rabbit reticulocyte lysate in vitro reactions with a coupled transcription/translation kit (PROMEGA, Wis.). Kumar, S., et al., J. Biol. Chem., 272:13548 (1997). Messenger RNA is preferred which originates from hematopoietic cells. Five µl aliquots of in vitro translated hematopoietic cell mRNA is incubated with 5–10 ng of recombinant E1 (SEQ ID NO:10) which is the translated structural coding region of human E1 ubiquitin activating enzyme Uba1), approximately 100 ng of E2 (E217k (SEQ ID NO:11 (structural coding region))) [The human version (Ubc2) is preferred as described by Koken, M., et al., PNAS, 88:8865 (1991)] (alternately, UBC2, UBC3, UBC4, UBC5, UBC6, UBC7, UBC8, UBC9, UBC$_{epi}$, UBC$_{bendless}$ (as per citations supra)), 200 ng of the novel human E3 ubiquitin protein ligase (e.g., SEQ ID NO:3), in 20 mM Tris-HCl, pH 7.6, 50 mM NaCl, 4 mM ATP, 10 mM MgCl2, and 0.2 mM dithiothreitol, for 2 hours at 30° C. One mg of glutathione-s-transferase (GST)-ubiquitin fusion protein is then added to 5 ml of translation reaction mixture and incubated for an additional 5 min at room temperature before the reaction is quenched with SDS/PAGE loading buffer. Reactions are terminated after 2 h. at 30° C by the addition of SDS-sample buffer. Samples are subject to boiling water heat for 5 mnin, resolved by SDS-PAGE, and visualized by autoradiography. Samples which contain the ubiquitin fusion protein demonstrate shift in the mobility of protein samples that are ubiquitinated.

Example III
Scintillation Proximity Assay (SPA)

Recombinant E1(using, e.g., SEQ ID NO:10), E2 (using, e.g., SEQ ID NO: 1 1) [The human version (Ubc2) is preferred as described by Koken, M., et al., PNAS, 88:8865 (1991)], and the novel human E3 ubiquitin protein ligase (using, e.g., SEQ ID NO:2) are used to develop a "mix and measure" 96-well SPA (AMERSHAM Scintillation Proximity Assay) by incorporating $^{125}$I-labeled mono-ubiquitin (AMERSHAM) onto a target protein substrate in the presence of ATP and MgCl$_2$. Histone 2A, troponin T, albumin, or α-actin, for example, may be used as target proteins. The ubiquitinated protein is detected using protein A-labeled SPA beads (AMERSHAM) and a polyclonal antibody to the target protein substrate in question. Both protein A-linked and avidin-linked SPA beads have been successfully used in assays using histone2A and biotinylated histone2A, separately, as substrates.

Ubiquitin (UBQ) SPA Assay Protocol

The reaction mixtures contain 50 mM Tris-HCl (pH 7.5), 2 mM ATP, 5mM MgCl$_2$, 0.5 mM DTT, (5 ng) recombinant E1 (expressed and isolated from SEQ ID NO:10), (10 ng) recombinant recombinant E2 (expressed and isolated from SEQ ID NO:11) [The human version (Ubc2) is preferred as described by Koken, M., et al., PNAS, 88:8865 (9199)], and (20 ng recombinant the novel human E3 ubiquitin protein ligase (expressed and isolated from SEQ ID NO:2), 1 µg $^{125}$I-Ubiquitin (AMERSHAM, Bucks, UK), and 2 µg of biotinylated Histone (SIGMA, St. Louis, Mo.) to give a final volume of 100 ml. Conjugation assays are performed at room temperature for 2 hours. Following incubation, reactions are terminated by addition of 10 mM EDTA and 0.1 mg/well avidin-linked SPA beads (AMERSHAM).

| Final concentrations | |
|---|---|
| | Final Concentration in assay |
| E1 | 5 ng/µl |
| E2 | 10 ng/µl |
| E3 | 20 ng/ul |
| Radiolabelled UBQ | 0.02 µCi/well |
| ATP | 2 mM |
| MgCl$_2$ | 5 mM |
| DTT | 0.5 mM |
| Bt-histone | 50 ng/µl |

Stock reagents
1) E1: @ 9.31 mg/ml
2) E2: @ 6.68 mg/ml
3) E3: @ 8.60 mg/ml
4) $^{125}$I-Ubiquitin: @ 0.1 µCi/µl
5) ATP: Make at 200 mM ie. 110.2 mg/ml in Tris buffer
6) MgCl$_2$: Make at 500 mM ie. 101.7 mg/ml in Tris buffer
7) DTT: Make at 1M ie. 154.2 mg/ml in Tris buffer
8) Bt-histone: 2 mg/ml
Buffer: 50 mM Tris-HCl pH 7.5
Preparation of Reagents
Addition 1 (E1E2/E3)
(In Tris buffer)
Dilute E1 1:745
Dilute E2 1:267
Dilute E3 1:96

| Addition 2 (Label/ATP/M2Cl2/DTT/Bt-histone) Add the following amounts per ml: (Make up with Tris buffer) | |
|---|---|
| | µl |
| Label | 4 |
| ATP | 20 |
| MgCl$_2$ | 20 |
| DTT | 1 |
| Bt-histone | 2 |

Biotinylation of Histone2A

Histone2A is biotinylated using BOEHRINGER MANNHEIM kit (Indianapolis, Ind. (cat. no 1418165)) according to the manufacturers instructions. Briefly, free amino groups of the target protein (histone2A in this case) are reacted with D-biotinyl-e-aminocaproic acid-N-hydroxysuccinimide ester (biotin-7-NHS) by forming a stable amide bond. Non-reacted biotin-7-NHS is separated on a Sephadex G-25 column. The precise molar concentrations used are 4 mg Histone2A in 1 ml of phosphate buffered saline to which added 20 mg/ml biotin-7-NHS is added the incubation is carried out at room temperature for 2 hours with gentle shaking.

| Stop Mix (Bead/EDTA) (Make up with Tris buffer) Add the following amounts per ml: | |
|---|---|
| | μl |
| Streptavidin SPA Bead | 600 |
| 500 mM EDTA | 200 |

Method
Use DYNATECH microlite 1 plates
Add 10 μl 300 mM EDTA to blank wells
Add 40 μl of Addition 1
Add 50 μl of Addition 2
Incubate at room temperature for 2 hours
Add 50 μl of Stop Mix
Leave overnight and count next day Example IV ELISA Assay Target proteins, e.g., histone2A, are fixed to the bottom of a 96-well ELISA plate in the presence of PEI (polyethylimine). The reaction mix: recombinant E1 (expressed and isolated from SEQ ID NO:10), recombinant recombinant E2 (expressed and isolated from SEQ ID NO:11) [The human version (Ubc2) is preferred as described by Koken, M., et al., PNAS, 88:8865 (1991)], and recombinant human E3 ubiquitin protein ligase (expressed and isolated from SEQ ID NO:2), mono-ubiquitin (SIGMA), ATP, and $MgCl_2$, is added to each well. Ubiquitinated target protein is detected using a horseradish peroxidase-linked polyclonal antibody to polyubiquitin. Horseradish peroxidase is detected using ATBS (2,2'-azino-di-[3-ethyl-benzthiazoline solfonate]) and ECL (enhanced chemiluminescence) detection systems. This assay may be used as a high throughput screen or as a secondary screen.

1. Coat plate with 100 μl of desired target protein substrate (e.g., histone2A) diluted in PBS (usually at approx. 1–10 μg/ml). Allow to stand overnight at room temperature or 2 hours at 37° C. (coated plates may be stored for at least 2 weeks at 4° C.).
2. Wash plate 3 times with ELISA Wash Buffer (PBS+ 0.05% Tween-20).
3. Add 150 μl of PBS containing 1% BSA to each well. Incubate at room temperature for 2 hours or at 37 degrees for 1 hour.
4. Wash plate 3 times with ELISA Wash Buffer.
5. Add 100 μl of antibody (e.g., Ub N-19, Santa Cruz, Biotechnology, Calif.) dilutions in PBS containing 1% BSA. Use normal mouse serum as a negative control for ascites and normal rabbit serum as a negative control for rabbit antisera.
6. Cover plate and incubate overnight at room temperature or a minimum of 2 hours at 37° C.
7. Wash plate 3 times with ELISA Wash Buffer.
8. Add 100 μl of the appropriate second antibody enzyme conjugate (e.g., Goat anti-rabbit IgG-HRP) diluted in PBS containing 1% BSA.
9. Cover plate and incubate a minimum of 4 hours at room temperature or 2 hours at 37° C.
10. Wash plate 3 times with ELISA Wash Buffer.

Horseradish Peroxidase (HRP) Substrate (or according to vendor's recommendation)

25 ml 0.1 Citrate-Phosphate buffer, pH5

5 g citric acid monohydrate 7 g Na2HPO4 anhydrous bring volume to 500 ml with dH2O Stopping Reagent: 6 N H2SO4, 50 ul/well Alkaline phosphatase Substrate (or according to vendor's recommendation)

1 tube PNPP (100 mg/ml, 0.2 ml)

20 ml diethanolamine-HCl pH 9.8/1 mM MgCl2

Stopping reagent: 1 M NaOH, 50 μl/well

Add 100 μl of substrate (orthophenyldiamine+substrate buffer+$H_2O_2$) (6 μl hydrogen peroxide; 10 mg OPD (orthophenyldiamine)); stop reaction when absorbancies in the mid-range of the titration reach about 2.0, or after 1 hour (whichever comes first).

12. Read plate at:
450 nm - HRP unstopped
492 nm - HRP stopped
405 nm - Alkaline phosphatase (Microplate Spectrophotometer System, Calif.)

See, Takada, K., et al., Eur. J. Biochem., 233:42 (1995); Takada, K., et al., Biochim. Biophys. Acta., 1290:282 (1996).

Example V

Northern Blots

Analysis of poly $A^+$ RNA's from human tissues is generally carried out using a panel of commercially available pre-blotted RNAs (Clontech Laboratories, Palo Alto, Calif.). Otherwise, Hybond-$N^+$, supplied by Amersham International PLC, AMERSHAM, Bucks, UK, supported nylon-66 membrane with a pore size of 0.45 microns, is used for the immobilisation of nucleic acids by either UV cross linking or dry heat. Probes are labelled with $^{32}P$ by random hexamer priming, and hybridisations are carried out in 0.28M sodium phosphate (pH 7.2), 5×Denharts solution, 10% dextran sulphate, 0.1% SDS at 65° C. Membranes are washed to a final stringency of 0.2×SSC,0.1% SDS at 65° C.

Poly $A^+$ mRNA is prepared directly from ~1×$10^8$ hematopoietic cells using a FastTrack mRNA isolation kit (INVITROGEN, Carlsbad, Calif.). Total tissue mRNA is prepared via polytron homogenisation in 4M guanidine isothiocyanate, 2.5 mM citrate, 0.5% Saccosyl, 100 mMb-mercaptoethanol, followed by centrifugation through 5.7M CsCl, 25 mM sodium acetate at 135,000 g. Poly-$A^+$ is obtained using FastTrack mRNA isolation kit (INVITROGEN).

SSC 0.15M NaCl+0.015M sodium cirate pH 7.0

Denhart's Reagent

Solution containing 0.02% bovine serum albumin, o.o2% Ficol 400,000 (a non-ionic synthetic polymer of sucrose, dialysed and lyophilised and having an approximate molecular weight of 400,000) and 0.02% polyvinyl pyrrolidone.

Example VI

Expression of GST Fusion Constructs

All E3 ligase GST constructs as well as the control pGEX-5x-3 GST vector alone were transformed into ME DH5α E. coli cells. Single colonies were grown overnight at 37° C. shaking at 225 rpm in 10 ml of LB containing 100

µg/ml of ampicillin. The next day, this 10-ml culture was diluted 10-fold to 100 ml in LB/amp and allowed to grow for an additional hour. Protein expression was induced by adding isopropyl-β-D-thiogalactoside (IPTG; Life Technologies, Gaithersburg, Md.) to a final concentration of 1 mM and cultured an additional 3 hours. Bacteria were harvested by centrifugation at 5000 rpm for 10 minutes. The bacterial pellet was re-suspended in 15 ml of TBS (50 mM Tris 8.0/150 mM NaCl) containing 0.5% Triton-X100 and 1 mM phenylmethylsulfonylfluoride (PMSF). This suspension was sonicated three times for 20 seconds. After sonication, cellular debris was removed by centrifugation at 10,000 rpm for 10 minutes. Subsequently 150 µl of milk-blocked glutathione sepharose 4B (Pharmacia) was added to the supernatant, and the mixture was rocked at 4° C. for 1 hour. The beads were then collected by centrifugation at 500×g for 5 minutes and washed three times with 10 ml of the same buffer as used for resuspension above. Protein concentrations were determined by electrophoresis on an 8% Tris glycine gel and staining with Coomassie blue. Fusion proteins were eluted from the beads by adding of 300 µl of elution buffer (10 mM reduced glutathione in 50 mM Tris-HCl pH 8.0), incubating at room temperature for 10 minutes, and centrifuging at 500 ×g for 5 minutes. Elution and centrifugation steps were repeated three times, and the resulting supernatants were pooled.

Example VII

Ubiquitination Assays

Ubiquination reactions were performed using a protocol based on the published procedure of Hatakeyama, et al, J. Biol. Chem., 272:15085 (1997). Reaction mix tures containing 0.5 µg of purified E3 ligase (SEQ ID NO:3) GST fusion protein, 1 µg of 6-His-tagged E2 enzyme (UBCH2 or UBCH7), 1 µg of 6-His-tagged E1enzyme, 10 µg of bovine ubiquitin (Sigma, St. Louis, Mo.), and 1 µl of crude lysate from DH5α E. coli cells in reaction buffer (20 mM Tris-HCl pH 7.5, 50 mM NaCl, 5 mM ATP, 5 mM MgCl2) were incubated at 30° C. for 2 hours. Reducing sample buffer containing 5% β-mercaptoethanot was added, and samples were resolved by SDS-PAGE, transferred to nitrocellulose membranes, and immunoblotted with a purified anti-ubiquitin antibody (Sigma) followed by a purified horseradish peroxidase-conjugated anti-rabbit antibody (Amersham, Bucks, UK) and development using chemluminescence (ECL; Amersham). Bacterial proteins from the crude lysate served as ubiquination substrates. The FIG. 2 results demonstrate that the recombinant human itch E3 ubiquitin ligase has ubiquitinating activity in in vitro assays. See, FIG. 2→DH5a bacteria lysates. 12% SDS-PAGE Primary Ab (anti-ubiquitin ). Secondary Ab (Anti-rabbit Ig). The Western blot was developed using the ECL system Amersham, Bucks, UK).

Example VIII

Dominant Negative Mutant Construct

A single amino acid change in the human itchy cDNA sequence, cysteine (TGT) to alanine (GCT), at SEQ ID NO:3 position 820 in the active site was made using the wild-type GST-itchy fusion construct in pGEX-5x-3 as template and the STRATAGENE QuikChange site-directed mutagenesis kit according to manufacturer's instructions. La Jolla, Calif. The primers used for the reaction were: upper:

5'-GGCTACCCAGAAGTCATACCGCTTT-
TAATCGCCTGGACCTGCCAC-3'(SEQ ID NO:14);

lower:

5'-GTGGCAGGTCCAGGCGATTAAAAGCGG-
TATGACTTCTGGGTAGCC-3' (SEQ ID NO:15).

PCR conditions were: 95° C. 30 seconds; 16 cycles of 95° C. 30 seconds, 55° C. 1 minute, and 68° C. 15 minutes; 68° C. 3 minutes. Sequencing of the construct determined that the amino acid substitution at position 820 was successfully accomplished. See, FIG. 3.

Example IX

Stimulation with PMA and Ionomycin

In order to evaluate the role of the SEQ ID NO:3 E3 ligase in the activation of human leukocytes, stimulation experiments were performed independently using peripheral blood mononuclear cells, Jurkat cells, and U937 cells. Peripheral blood monocytes were isolated by layering whole blood diluted 1:1 with PBS onto 1.077 density Ficoll-Hypaque for fractionation and centrifuging at 400×g for 30 minutes. The cells at the interface were isolated, washed two times with PBS, and counted. Approximately 45×10$^6$ cells were used for each timepoint (unstimulated, 2 hours, 8 hours, 24 hours). Jurkat cells and U937 cells were counted, then washed twice with PBS. Approximately 90×10$^6$ cells were used for each timepoint. After determining cells counts, the appropriate number of cells was resuspended in OptiMEM media (Gibco) in 6-well tissue culture dishes. Cells were stimulated with 100 ng/ml PMA and I mM ionomycin for the specified times. After stimulation, cells were collected by low-speed centrifugation and lysed to isolate either protein for Western blot analysis (FIG. 4) or RNA for northern blotting using the RNeasy kit (Qiagen, Valencia, Calif.) (FIG. 5).

Figure 4:
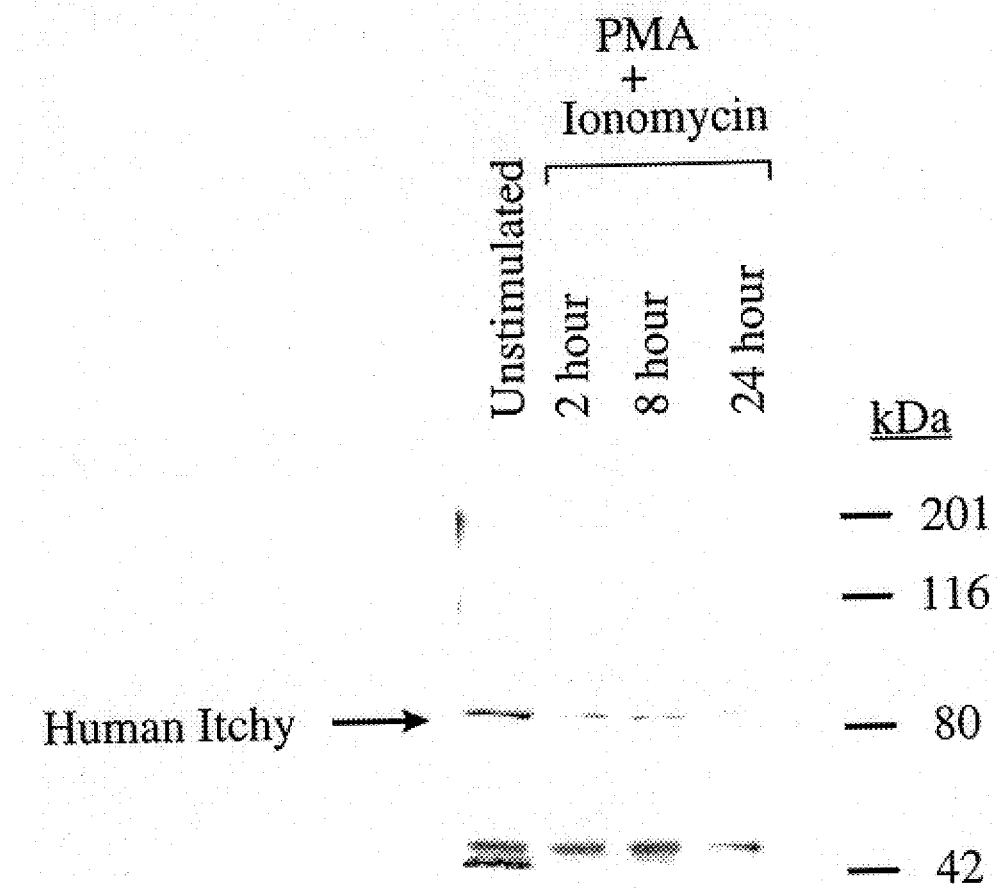
FIG. 4 demonstrates a marked decline in the intracellular SEQ ID NO:3 levels 2 h after activation of the jurkat T cells by PMA and ionomycin.
Figure 5:
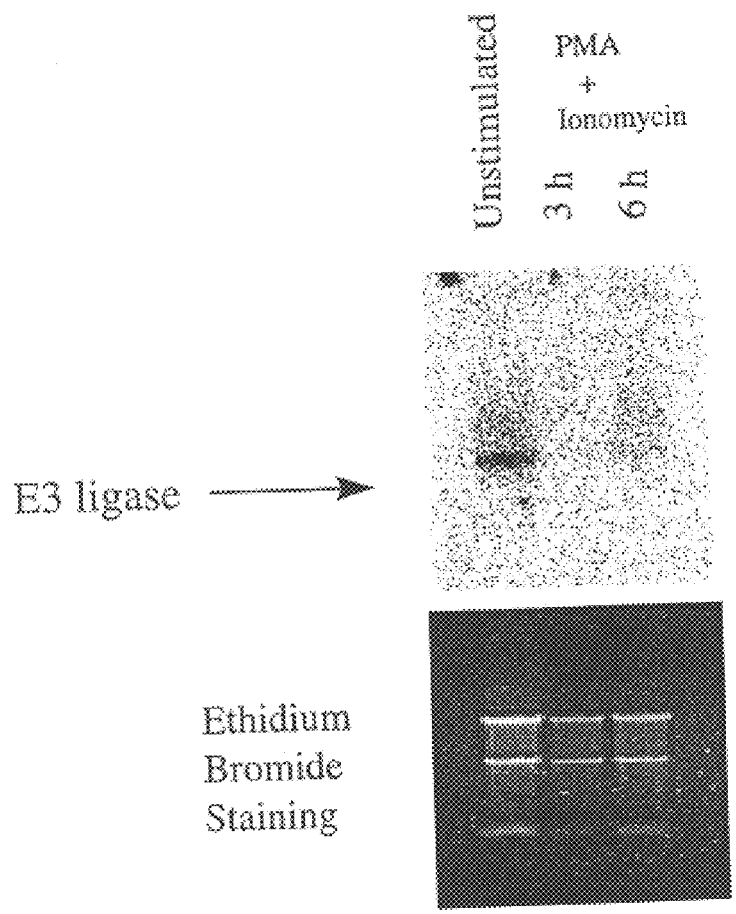
FIG. 5 demonstrates a dramatic decline in the level of human itchy E3 ligase mRNA within 3 h after stimulation of PBMC's.

Western Blot Analysis (FIG. 4)

Approximately 50×10$^6$ jurkat T cells were collected by low speed centrifugation for 5 minutes at room temperature. Cells were washed twice with PBS and resuspended in 100 µl of ice-cold lysis buffer (10 m-M Tris-HCl pH 7.2, 150 mM NaCl, 1% Triton-X100, 1% sodium deoxycholate, 0. 1% SDS, 1 mM PMSF, 1×COMPLETE protease inhibitors (Boerhinger Mannheim) and put on ice for 15 minutes. Cell debris was removed by centrifugation at 14,000 rpm at 4 C for 10 minutes. Supernatant was subsequently removed to a fresh tube, and protein concentration was estimated based on the number of cells lysed or was determined using the BioRad Protein Assay kit. Lysate aliquots corresponding to the desired protein concentration were mixed with equal volumes of reducing sample buffer containing 5% β-mercaptoethanol and boiled for 5 minutes. The samples were loaded on 10–12% Tris glycine PAGE gels (Novex, San Diego, Calif.) at 35 mA for approximately 1 hour. Proteins were transferred to nitrocellulose membranes, immunoblotted using an anti-peptide antibody described herein and a horseradish peroxidase-conjugated anti-rabbit secondary antibody (Amersham, Bucks, UK), and developed using Amersham ECL detection reagents and exposing to Hyperfilm-ECL (Amersham). To determine if the human itchy E3 ligase levels change after T cell activation, Jurkat T cells were activated by PMA and ionomycin and protein levels analyzed by Western blot analysis. There was a marked decline in the SEQ ID NO:3 levels 2 h after activation of the jurkat T cells. As activation of T lymphocytes by PMA and ionomycin results in a signal transduction cascade, these findings suggest that the SEQ ID NO:3 'itchy' E3 ligase is involved in turnover of signal transduction proteins in the lymphocytic cells. See, FIG. 4.

Northern Blot Analysis (FIG. 5)

20 mg total RNA samples were electroporesed on 1% denaturing formaldehyde agarose gels in MOPS buffer (Sambrook, et al., Molecular Cloning, A Laboratory Manual, CSH( 1989)) and transferred onto hybond N+ (Amersham). Probes were labelled with $^{32}$P by random hexamer priming, and hybridisations were carried out in 0.28M sodium phosphate (pH 7.2), 5×Denharts solution, 10% dextran sulphate, 0.1% SDS at 65° C. Membranes were washed to a final stringency of 0.2×SSC,0.1% SDS at 65° C. To control loading variations, blots were stripped after autoradiography by boiling in 0.1% SDS, and then rehybridised using a probe containing 1.2 kb of a rat glyceraldehyde-3-phosphate dehydrogenase cDNA (GAPDH). Analysis of poly A+ RNA's from human tissues was carried out using a panel of commercially available pre-blotted RNAs (Clontech, Palo Alto, Calif.). The results demonstrate that the human itchy E3 ligase mRNA levels dramatically decline within 3 h after stimulation of PBMC's. These results suggest that the 'itchy' E3 ligase gene is involved in turnover of signal transduction molecules in the hematopoietic lineages. See, FIG. 5.

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A purified polynucleotide comprising a nucleic acid sequence which encodes a polypeptide comprising an amino acid sequence having at least about 80% homology to SEQ ID NO:3 and comprising at least one amino acid, relative to the position of SEQ ID NO:3, selected from the group consisting of V66, H70, A89, V108, G113, I122, I127, L134, S136, T145, A150, S151, S157, S159, K160, E162, D171, D175, G177, A178, R182, V184, S185, A225, T226, E228, N245, P271, T273, S380, T452, D650, and A752.

2. A purified polynucleotide comprising a nucleic acid sequence which encodes a E3 ubiquitin protein ligase polypeptide comprising an amino acid sequence having at least about 96% homology to SEQ ID NO:3.

3. A purified polynucleotide according to claim 2 comprising a nucleic acid sequence which encodes a E3 ubiquitin protein ligase polypeptide comprising an amino acid sequence having at least about 96% homology to SEQ ID NO:3 and comprising at least one amino acid, relative to the position of SEQ ID NO:3, selected from the group consisting of V66, H70, A89, V108, G113, I122, I127, L134, S 136, T145, A150, S151, S157, S159, K160, E162, D171, D175, G177, A178, R182, V184, S185, A225, T226, E228, N245, P271, T273, S380, T452, D650, and A752.

4. A polynucleotide according to claim 1 or claim 2 which encodes a dominant negative mutant polypeptide wherein cysteine at position 820 (C820), relative to SEQ ID NO:3, is substituted or deleted.

5. The polynucleotide of claim 1 wherein the polynucleotide sequence comprises the sequence as depicted in SEQ ID NO:2.

6. An antisense molecule comprising an oligomer from about 12 to 25 nucleotides in length which is complementary to SEQ ID NO:1.

7. An expression vector comprising the polynucleotide of claim 1 or claim 2.

8. A host cell transformed with the expression vector of claim 7.

9. An in vitro method of identifying a compound that modulates a biological activity of an E3 ubiquitin protein ligase polypeptide which is encoded by the polynucleotide of claim 1 or claim 2, comprising:

(a) combining a candidate compound modulator with the polypeptide and measuring an effect of the candidate compound modulator on the biological activity of the polypeptide.

10. An in vitro method of identifying compounds that modulate a biological activity of a E3 ubiquitin protein ligase polypeptide according to claim 9, comprising:

(a) combining a candidate compound modulator with a host-cell which expresses said polypeptide, and (b) measuring an effect of the candidate compound modulator on the biological activity of the polypeptide.

11. A method of modulating a biological activity of a E3 ubiquitin protein ligase polypeptide in a cell in vitro comprising administering an effective amount of a polynucleotide according to claim 4 to said cell.

12. A method of modulating a biological activity of an E3 ubiquitin protein ligase polypeptide in a cell in vitro comprising administering an effective amount of a polypeptide according to claim 6 to said cell.

* * * * *

SEQUENCE LISTING

```
<160> NUMBER OF SEQ ID NOS: 15

<210> SEQ ID NO 1
<211> LENGTH: 5372
<212> TYPE: DNA
<213> ORGANISM: Homo sapiens

<400> SEQUENCE: 1
tcgccgccgc cccgagtccc ggtaccatgc atttcacggt ggccttgtgg agacaacgcc      60
ttaacccaag gaagtgactc aaactgtgag aacttcaggt tttccaacct attggtggta     120
tgtctgacag tggatcacaa cttggttcaa tgggtagcct caccatgaaa tcacagcttc     180
agatcactgt catctcagca aaacttaagg aaaataagaa gaattggttt ggaccaagtc     240
cttacgtaga ggtcacagta gatggacagt caaagaagac agaaaaatgc aacaacacaa     300
acagtcccaa gtggaagcaa ccccttacag ttatcgttac ccctgtgagt aaattacatt     360
ttcgtgtgtg gagtcaccag acactgaaat ctgatgtttt gttgggaact gctgcattag     420
atatttatga aacattaaag tcaaacaata tgaaacttga agaagtagtt gtgactttgc     480
agcttggagg tgacaaagag ccaacagaga cataggagaa cttgtcaatt tgtcttgatg     540
ggctacagtt agagtctgaa gttgttacca atggtgaaac tacatgttca gaaagtgctt     600
ctcagaatga tgatggctcc agatccaagg atgaaacaag agtgagcaca aatggatcag     660
atgaccctga agatgcagga gctggtgaaa ataggagagt cagtgggaat aattctccat     720
cactctcaaa tggtggtttt aaaccttcta gacctccaag accttcacga ccaccaccac     780
ccaccccacg tagaccagca tctgtcaatg gttcaccatc tgccacttct gaaagtgatg     840
ggtctagtac aggctctctg ccgccgacaa atacaaatac aaatacatct gaaggagcaa     900
catctggatt aataattcct cttactatat ctggaggctc aggccctagg ccattaaatc     960
ctgtaactca agctcccttg ccacctggtt gggagcagag agtggaccag cacgggcgag    1020
tttactatgt agatcatgtt gagaaaagaa caacatggga tagaccagaa cctctacctc    1080
ctggctggga acggcgggtt gacaacatgg gacgtattta ttatgttgac catttcacaa    1140
gaacaacaac gtggcagagg ccaacactgg aatccgtccg gaactatgaa caatggcagc    1200
tacagcgtag tcagcttcaa ggagcaatgc agcagtttaa ccagagattc atttatggaa    1260
atcaagattt atttgctaca tcacaaagta aagaatttga tcctcttggt ccattgccac    1320
ctggatggga agagaaca gacagcaatg gcagagtata tttcgtcaac cacaacacac    1380
```

-continued

```
gaattacaca atgggaagac cccagaagtc aaggtcaatt aaatgaaaag cccttacctg    1440
aaggttggga aatgagattc acagtggatg gaattccata ttttgtggac cacaatagaa    1500
gaactaccac ctatatagat ccccgcacag gaaaatctgc cctagacaat ggacctcaga    1560
tagcctatgt tcgggacttc aaagcaaagg ttcagtattt ccggttctgg tgtcagcaac    1620
tggccatgcc acagcacata aagattacag tgacaagaaa aacattgttt gaggattcct    1680
ttcaacagat aatgagcttc agtccccaag atctgcgaag acgtttgtgg gtgatttttc    1740
caggagaaga aggtttagat tatggagtg tagcaagaga atggttcttt cttttgtcac     1800
atgaagtgtt gaacccaatg tattgcctgt ttgaatatgc agggaaggat aactactgct    1860
tgcagataaa ccccgcttct tacatcaatc cagatcacct gaaatatttt cgttttattg    1920
gcagatttat tgccatggct ctgttccatg ggaaattcat agacacgggt ttttctttac    1980
cattctataa gcgtatcttg aacaaaccag ttggactcaa ggatttagaa tctattgatc    2040 cagaattta caattctctc atctgggtta aggaaaacaa tattgaggaa tgtgatttgg     2100
aaatgtactt ctccgttgac aaagaaattc taggtgaaat taagagtcat gatctgaaac    2160
ctaatggtgg caatattctt gtaacagaag aaaataaaga ggaatacatc agaatggtag    2220
ctgagtggag gttgtctcga ggtgttgaag aacagacaca agctttcttt gaaggcttta    2280
atgaaattct tccccagcaa tatttgcaat actttgatgc aaaggaatta gaggtccttt    2340
tatgtggaat gcaagagatt gatttgaatg actggcaaag acatgccatc taccgtcatt    2400
atgcaaggac cagcaaacaa atcatgtggt tttggcagtt tgttaaagaa attgataatg    2460
agaagagaat gagacttctg cagtttgtta ctggaacctg ccgattgcca gtaggaggat    2520
ttgctgatct catggggagc aatggaccac agaaattctg cattgaaaaa gttgggaaag    2580
aaaattggct acccagaagt catacctgtt ttaatcgcct ggacctgcca ccatacaaga    2640
gctatgagca actgaaggaa aagctgttgt ttgccataga agaaacagaa ggatttggac    2700
aagagtaact tctgagaact tgcaccatga atgggcaaga acttatttgc aatgtttgtc    2760
cttctctgcc tgttgcacat cttgtaaaat tggacaatgg ctctttagag agttatctga    2820
gtgtaagtaa attaatgttc tcatttagat ttatctccca gtgatttcta ctcagcgttt    2880
ccagaaatca ggtctgcaaa tgactagtca gaaccttgct taacatgaga ttttaacaca    2940
acaatgaaat ttgccttgtc ttattccact agtttattcc tttaacaaca atattttatg    3000
tgtatcaaaa gtctcacttg ggagtagtgt tttttcttt tagacattct gcagacatgc     3060
agggaagtcc tttggtaact gcaatataca agattttcct attaagcctc ttggtaagag    3120
gcatttgtta aaagtgcaag cttactcctg cttctgggga tgtgagcaaa attcgggctt    3180
gtgttctccc tctcatttta gtctgacttg actattgttt ttcctttctg gcgcatgaat    3240
ccatacatca ttcctggaag tgaggcaaga ctcttgcatc tctacaaagt agttttgtca    3300
atttgaattc agggaaaagt tggtcacagc ctgcaaatga cttcatttgg aagtctgatt    3360
gtttcagttg cctgacaaat actacacttt acaaacaatg ttaacactgt gattccttca    3420
ttgttttaag aagttaacct agggccgggc atggtggctc atacctgtaa tcctagcact    3480
ctgggaggcc gaggcaggag gatcccttta gcccaggagt taaagaccag cctgggcaac    3540 ataggagac cctgtctttt ttttgggcag cgtggtgggg gataaataaa waaaarraaa     3600
aaaaacktag cctagaatta gaattaattt aattgaattc atctaaagat gtctctggtg    3660 attttatat gttccgctat ataattgatg ctttatagtt ttatcataat ccaacaactt     3720
```

-continued

```
cagttatatt taattattgt taaggagttt aagactagaa agactagagt gctttctagt    3780
ccaaatagag gtcagtgaaa cagcttttga catcagattt tcatttgaga gggagagctg    3840
tggtactggc taaaagaaa ggaagataac atccagtaac cacaggaata tattctctgt    3900
gaattaaaag tcttcaaagt tatcatttct ctgacatatg ttggagtagt catttccatt    3960
ctttacattg tcatgaactg gattgataac cctcatctgc aatattttca cccctaaaat    4020
ttttaacagg gtttcctttt tttctcacga ctatttaagt ttagattgct ccattattaa    4080
ctgattaatg cactttgaag ttctctggaa ttaattattt taacttggcc tagcttcgac    4140
tgtcaaggtg gctgttataa atttgacttc attggcagtg gatgaagcct aagccagctg    4200
agtctctatc atagctgaac cctgaggaca gcctcatagc tcatgtatca gggacttttg    4260
ccacatttca gaggcatagc atgaacaagt aatattaagc caagaataag cagcagaacc    4320
ctgttccata tggaaaaaag aaaaacaatt ttttgtccct aatgttcttc cttttacatc    4380
ctggaacaac aataaaaaca ttttttttaaa cttgtctact gtaagatact gccatcataa    4440
agcagagact tacatgagtg aaagggttgc ctcatcaagc agctcagtgt aaatggggag    4500
gctaggctct ccccagccct atggtttttt tatttcatgt accccaggaa atactgtgtg    4560
gtttctaaaa gccctggttg ttaaaagtag ggactctgcc tttttgttgg tagggagaaa    4620
aaacgctatt gctttgtctt acagagcgaa tgtctgccaa ctacccgttc attatataag    4680
tctgaacttg gtaatatatg gctaatgaag attaagccct ctataaagac ttcctgttga    4740
ggtgaattct catactgaaa tgtagttacc tacaatattt actagagatt tatgaaatta    4800
aattaagaga taatgtaaga aaatacattt tttttggttc tatataatgc ttcatgattc    4860
atttagggac ctagaaatat tgtgtgaaaa tatataaata tcacccaaaa ggctttctgc    4920
cctatatttt taaaatacag aatagttata tttgaagtag ccctggccct agttctatag    4980
ggcttggcta tttaatattt ttatggaaga agtgtttagt tctggaaaag gtaaatgctt    5040
gtatatatat ttttgcagcc tgggatctcc ctactccatt ttttccttta atttaagtgg    5100
ccacatgtat atgtcttccc tgctgtgtta ggaaaatggg ggctggatat cccaagaatc    5160
agaggttata taaaaatact gcaaatagac cgcagacata aatatctacc aaatgctatc    5220
ttaaattttg gtccaaactg aacatatgga aatagattta ttgtaagtat ttacttagag    5280
ctttttctta aatctgaact aacttgcttt tagaagtctt tttctttgta agcattgtaa    5340
atgctaataa atcctgttaa ttttttttttt tt                                5372
```

<210> SEQ ID NO 2
<211> LENGTH: 2559
<212> TYPE: DNA
<213> ORGANISM: Homo sapiens

<400> SEQUENCE: 2

```
atgggtagcc tcaccatgaa atcacagctt cagatcactg tcatctcagc aaaacttaag     60
gaaaataaga agaattggtt tggaccaagt ccttacgtag aggtcacagt agatggacag    120
tcaaagaaga cagaaaaatg caacaacaca acagtccca agtggaagca ccccttaca     180 gttatcgtta cccctgtgag taaattacat tttcgtgtgt ggagtcacca gacactgaaa    240
tctgatgttt tgttgggaac tgctgcatta gatatttatg aaacattaaa gtcaaacaat    300 atgaacttg aagaagtagt tgtgactttg cagcttggag gtgacaaaga gccaacagag    360
acaataggag acttgtcaat ttgtcttgat gggctacagt tagagtctga agttgttacc    420
aatggtgaaa ctacatgttc agaaagtgct tctcagaatg atgatggctc cagatccaag    480
```

```
gatgaaacaa gagtgagcac aaatggatca gatgaccctg aagatgcagg agctggtgaa    540
aataggagag tcagtgggaa taattctcca tcactctcaa atggtggttt taaaccttct    600
agacctccaa gaccttcacg accaccacca cccacccca gtagaccagc atctgtcaat    660
ggttcaccat ctgccacttc tgaaagtgat gggtctagta caggctctct gccgccgaca    720
aatacaaata caaatacatc tgaaggagca acatctggat taataattcc tcttactata    780
tctggaggct caggccctag gccattaaat cctgtaactc aagctcccttg gccacctggt   840 tgggagcaga gagtggacca gcacgggcga gtttactatg tagatcatgt tgagaaaaga   900
acaacatggg atagaccaga acctctacct cctggctggg aacggcgggt tgacaacatg    960
ggacgtattt attatgttga ccatttcaca agaacaacaa cgtggcagag gccaacactg   1020
gaatccgtcc ggaactatga acaatggcag ctacagcgta gtcagcttca aggagcaatg   1080
cagcagttta accagagatt catttatggg aatcaagatt tatttgctac atcacaaagt   1140
aaagaatttg atcctcttgg tccattgcca cctggatggg agaagagaac agacagcaat   1200
ggcagagtat atttcgtcaa ccacaacaca cgaattacac aatgggaaga ccccagaagt   1260
caaggtcaat taaatgaaaa gcccttacct gaaggttggg aaatgagatt cacagtggat   1320
ggaattccat attttgtgga ccacaataga gaaactacca cctatataga tccccgcaca   1380
ggaaaatctg ccctagacaa tggacctcag atagcctatg ttcgggactt caaagcaaag   1440
gttcagtatt tccggttctg tgtgcagcaa ctggccatgc cacagcacat aaagattaca   1500
gtgacaagaa aaacattgtt tgaggattcc tttcaacaga taatgagctt cagtccccaa   1560
gatctgcgaa gacgtttgtg ggtgattttt ccaggagaag aaggtttaga ttatggaggt   1620
gtagcaagag aatggttctt tcttttgtca catgaagtgt tgaacccaat gtattgcctg   1680
tttgaatatg cagggaagga taactactgc ttgcagataa accccgcttc ttacatcaat   1740
ccagatcacc tgaaatattt tcgttttatt ggcagattta ttgccatggc tctgttccat   1800
gggaaattca tagacacggg ttttttcttta ccattctata gcgtatcttg aacaaaacca   1860
gttggactca aggatttaga atctattgat ccagaatttt acaattctct catctgggtt   1920
aaggaaaaca atattgagga atgtgatttg gaaatgtact tctccgttga caaagaaatt   1980
ctaggtgaaa ttaagagtca tgatctgaaa cctaatggtg caatattctt gtaacagaa    2040 gaaaataaag aggaatacat cagaatggta gctgagtgga ggttgtctcg aggtgttgaa   2100
gaacagacac aagctttctt tgaaggcttt aatgaaattc ttccccagca atatttgcaa   2160
tactttgatg caaaggaatt agaggtcctt ttatgtggaa tgcaagagat tgatttgaat   2220
gactggcaaa gacatgccat ctaccgtcat tatgcaagga ccagcaaaca aatcatgtgg   2280
ttttggcagt tgttaaaga aattgataat gagaagagaa tgagacttct gcagtttgtt    2340 actgaacct gccgattgcc agtaggagga tttgctgatc tcatggggag caatggacca   2400
cagaaattct gcattgaaaa agttgggaaa gaaaattggc tacccagaag tcatacctgt   2460
tttaatcgcc tggacctgcc accatacaag agctatgagc aactgaagga aaagctgttg   2520
tttgccatag aagaaacaga aggatttgga caagagtaa                          2559
```

<210> SEQ ID NO 3
<211> LENGTH: 852
<212> TYPE: PRT
<213> ORGANISM: Homo sapiens

<400> SEQUENCE: 3

-continued

```
Met Gly Ser Leu Thr Met Lys Ser Gln Leu Gln Ile Thr Val Ile Ser
 1               5                  10                  15

Ala Lys Leu Lys Glu Asn Lys Lys Asn Trp Phe Gly Pro Ser Pro Tyr
            20                  25                  30

Val Glu Val Thr Val Asp Gly Gln Ser Lys Thr Glu Lys Cys Asn
            35                  40                  45

Asn Thr Asn Ser Pro Lys Trp Lys Gln Pro Leu Thr Val Ile Val Thr
 50                      55                  60

Pro Val Ser Lys Leu His Phe Arg Val Trp Ser His Gln Thr Leu Lys
 65                  70                  75                  80

Ser Asp Val Leu Leu Gly Thr Ala Ala Leu Asp Ile Tyr Glu Thr Leu
                85                  90                  95

Lys Ser Asn Asn Met Lys Leu Glu Glu Val Val Thr Leu Gln Leu
                100                 105                 110

Gly Gly Asp Lys Glu Pro Thr Glu Thr Ile Gly Asp Leu Ser Ile Cys
            115                 120                 125

Leu Asp Gly Leu Gln Leu Glu Ser Glu Val Val Thr Asn Gly Glu Thr
130                 135                 140

Thr Cys Ser Glu Ser Ala Ser Gln Asn Asp Asp Gly Ser Arg Ser Lys
145                 150                 155                 160

Asp Glu Thr Arg Val Ser Thr Asn Gly Ser Asp Asp Pro Glu Asp Ala
            165                 170                 175

Gly Ala Gly Glu Asn Arg Arg Val Ser Gly Asn Asn Ser Pro Ser Leu
            180                 185                 190

Ser Asn Gly Gly Phe Lys Pro Ser Arg Pro Pro Arg Pro Ser Arg Pro
            195                 200                 205

Pro Pro Pro Thr Pro Arg Arg Pro Ala Ser Val Asn Gly Ser Pro Ser
210                 215                 220

Ala Thr Ser Glu Ser Asp Gly Ser Ser Thr Gly Ser Leu Pro Pro Thr
225                 230                 235                 240

Asn Thr Asn Thr Asn Thr Ser Glu Gly Ala Thr Ser Gly Leu Ile Ile
                245                 250                 255

Pro Leu Thr Ile Ser Gly Gly Ser Gly Pro Arg Pro Leu Asn Pro Val
                260                 265                 270

Thr Gln Ala Pro Leu Pro Pro Gly Trp Glu Gln Arg Val Asp Gln His
            275                 280                 285

Gly Arg Val Tyr Tyr Val Asp His Val Glu Lys Arg Thr Thr Trp Asp
290                 295                 300

Arg Pro Glu Pro Leu Pro Pro Gly Trp Glu Arg Arg Val Asp Asn Met
305                 310                 315                 320

Gly Arg Ile Tyr Tyr Val Asp His Phe Thr Arg Thr Thr Thr Trp Gln
                325                 330                 335

Arg Pro Thr Leu Glu Ser Val Arg Asn Tyr Glu Gln Trp Gln Leu Gln
            340                 345                 350

Arg Ser Gln Leu Gln Gly Ala Met Gln Gln Phe Asn Gln Arg Phe Ile
            355                 360                 365

Tyr Gly Asn Gln Asp Leu Phe Ala Thr Ser Gln Ser Lys Glu Phe Asp
            370                 375                 380

Pro Leu Gly Pro Leu Pro Pro Gly Trp Glu Lys Arg Thr Asp Ser Asn
385                 390                 395                 400

Gly Arg Val Tyr Phe Val Asn His Asn Thr Arg Ile Thr Gln Trp Glu
            405                 410                 415

Asp Pro Arg Ser Gln Gly Gln Leu Asn Glu Lys Pro Leu Pro Glu Gly
```

-continued

```
                420             425             430
Trp Glu Met Arg Phe Thr Val Asp Gly Ile Pro Tyr Phe Val Asp His
            435             440             445
Asn Arg Arg Thr Thr Thr Tyr Ile Asp Pro Arg Thr Gly Lys Ser Ala
450             455             460
Leu Asp Asn Gly Pro Gln Ile Ala Tyr Val Arg Asp Phe Lys Ala Lys
465             470             475             480
Val Gln Tyr Phe Arg Phe Trp Cys Gln Gln Leu Ala Met Pro Gln His
                485             490             495
Ile Lys Ile Thr Val Thr Arg Lys Thr Leu Phe Glu Asp Ser Phe Gln
            500             505             510
Gln Ile Met Ser Phe Ser Pro Gln Asp Leu Arg Arg Leu Trp Val
            515             520             525
Ile Phe Pro Gly Glu Glu Gly Leu Asp Tyr Gly Val Ala Arg Glu
530             535             540
Trp Phe Phe Leu Leu Ser His Glu Val Leu Asn Pro Met Tyr Cys Leu
545             550             555             560
Phe Glu Tyr Ala Gly Lys Asp Asn Tyr Cys Leu Gln Ile Asn Pro Ala
                565             570             575
Ser Tyr Ile Asn Pro Asp His Leu Lys Tyr Phe Arg Phe Ile Gly Arg
            580             585             590
Phe Ile Ala Met Ala Leu Phe His Gly Lys Phe Ile Asp Thr Gly Phe
            595             600             605
Ser Leu Pro Phe Tyr Lys Arg Ile Leu Asn Lys Pro Val Gly Leu Lys
            610             615             620
Asp Leu Glu Ser Ile Asp Pro Glu Phe Tyr Asn Ser Leu Ile Trp Val
625             630             635             640
Lys Glu Asn Asn Ile Glu Glu Cys Asp Leu Glu Met Tyr Phe Ser Val
                645             650             655
Asp Lys Glu Ile Leu Gly Glu Ile Lys Ser His Asp Leu Lys Pro Asn
                660             665             670
Gly Gly Asn Ile Leu Val Thr Glu Glu Asn Lys Glu Glu Tyr Ile Arg
            675             680             685
Met Val Ala Glu Trp Arg Leu Ser Arg Gly Val Glu Glu Gln Thr Gln
690             695             700
Ala Phe Phe Glu Gly Phe Asn Glu Ile Leu Pro Gln Gln Tyr Leu Gln
705             710             715             720
Tyr Phe Asp Ala Lys Glu Leu Glu Val Leu Leu Cys Gly Met Gln Glu
                725             730             735
Ile Asp Leu Asn Asp Trp Gln Arg His Ala Ile Tyr Arg His Tyr Ala
            740             745             750
Arg Thr Ser Lys Gln Ile Met Trp Phe Trp Gln Phe Val Lys Glu Ile
            755             760             765
Asp Asn Glu Lys Arg Met Arg Leu Leu Gln Phe Val Thr Gly Thr Cys
770             775             780
Arg Leu Pro Val Gly Gly Phe Ala Asp Leu Met Gly Ser Asn Gly Pro
785             790             795             800
Gln Lys Phe Cys Ile Glu Lys Val Gly Lys Glu Asn Trp Leu Pro Arg
                805             810             815
Ser His Thr Cys Phe Asn Arg Leu Asp Leu Pro Pro Tyr Lys Ser Tyr
            820             825             830
Glu Gln Leu Lys Glu Lys Leu Leu Phe Ala Ile Glu Glu Thr Glu Gly
            835             840             845
```

Phe Gly Gln Glu
    850

<210> SEQ ID NO 4
<211> LENGTH: 854
<212> TYPE: PRT
<213> ORGANISM: Mus musculus

<400> SEQUENCE: 4

Met Gly Ser Leu Thr Met Lys Ser Gln Leu Gln Ile Thr Val Ile Ser
1               5                   10                  15

Ala Lys Leu Lys Glu Asn Lys Lys Asn Trp Phe Gly Pro Ser Pro Tyr
            20                  25                  30

Val Glu Val Thr Val Asp Gly Gln Ser Lys Lys Thr Glu Lys Cys Asn
        35                  40                  45

Asn Thr Asn Ser Pro Lys Trp Lys Gln Pro Leu Thr Val Ile Val Thr
    50                  55                  60

Pro Thr Ser Lys Leu Cys Phe Arg Val Trp Ser His Gln Thr Leu Lys
65                  70                  75                  80

Ser Asp Val Leu Leu Gly Thr Ala Gly Leu Asp Ile Tyr Glu Thr Leu
                85                  90                  95

Lys Ser Asn Asn Met Lys Leu Glu Glu Val Val Met Thr Leu Gln Leu
            100                 105                 110

Val Gly Asp Lys Glu Pro Thr Glu Thr Met Gly Asp Leu Ser Val Cys
        115                 120                 125

Leu Asp Gly Leu Gln Val Glu Ala Glu Val Val Thr Asn Gly Glu Thr
    130                 135                 140

Ser Cys Ser Glu Ser Thr Thr Gln Asn Asp Asp Gly Cys Arg Thr Arg
145                 150                 155                 160

Asp Asp Thr Arg Val Ser Thr Asn Gly Ser Glu Asp Pro Glu Val Ala
                165                 170                 175

Ala Ser Gly Glu Asn Lys Arg Ala Asn Gly Asn Asn Ser Pro Ser Leu
            180                 185                 190

Ser Asn Gly Gly Phe Lys Pro Ser Arg Pro Pro Arg Pro Ser Arg Pro
        195                 200                 205

Pro Pro Pro Thr Pro Arg Arg Pro Ala Ser Val Asn Gly Ser Pro Ser
    210                 215                 220

Thr Asn Ser Asp Ser Asp Gly Ser Ser Thr Gly Ser Leu Pro Pro Thr
225                 230                 235                 240

Asn Thr Asn Val Asn Thr Ser Thr Ser Glu Gly Ala Thr Ser Gly Leu
                245                 250                 255

Ile Ile Pro Leu Thr Ile Ser Gly Gly Ser Gly Pro Arg Pro Leu Asn
            260                 265                 270

Thr Val Ser Gln Ala Pro Leu Pro Pro Gly Trp Glu Gln Arg Val Asp
        275                 280                 285

Gln His Gly Arg Val Tyr Tyr Val Asp His Val Glu Lys Arg Thr Thr
    290                 295                 300

Trp Asp Arg Pro Glu Pro Leu Pro Pro Gly Trp Glu Arg Arg Val Asp
305                 310                 315                 320

Asn Met Gly Arg Ile Tyr Tyr Val Asp His Phe Thr Arg Thr Thr Thr
                325                 330                 335

Trp Gln Arg Pro Thr Leu Glu Ser Val Arg Asn Tyr Glu Gln Trp Gln
            340                 345                 350

Leu Gln Arg Ser Gln Leu Gln Gly Ala Met Gln Gln Phe Asn Gln Arg

-continued

```
            355                 360                 365
    Phe Ile Tyr Gly Asn Gln Asp Leu Phe Ala Thr Ser Gln Asn Lys Glu
        370                 375                 380

Phe Asp Pro Leu Gly Pro Leu Pro Pro Gly Trp Glu Lys Arg Thr Asp
    385                 390                 395                 400

Ser Asn Gly Arg Val Tyr Phe Val Asn His Asn Thr Arg Ile Thr Gln
                    405                 410                 415

Trp Glu Asp Pro Arg Ser Gln Gly Gln Leu Asn Glu Lys Pro Leu Pro
                420                 425                 430

Glu Gly Trp Glu Met Arg Phe Thr Val Asp Gly Ile Pro Tyr Phe Val
            435                 440                 445

Asp His Asn Arg Arg Ala Thr Thr Tyr Ile Asp Pro Arg Thr Gly Lys
        450                 455                 460

Ser Ala Leu Asp Asn Gly Pro Gln Ile Ala Tyr Val Arg Asp Phe Lys
    465                 470                 475                 480

Ala Lys Val Gln Tyr Phe Arg Phe Trp Cys Gln Gln Leu Ala Met Pro
                    485                 490                 495

Gln His Ile Lys Ile Thr Val Thr Arg Lys Thr Leu Phe Glu Asp Ser
                500                 505                 510

Phe Gln Gln Ile Met Ser Phe Ser Pro Gln Asp Leu Arg Arg Arg Leu
            515                 520                 525

Trp Val Ile Phe Pro Gly Glu Glu Gly Leu Asp Tyr Gly Gly Val Ala
        530                 535                 540

Arg Glu Trp Phe Phe Leu Leu Ser His Glu Val Leu Asn Pro Met Tyr
    545                 550                 555                 560

Cys Leu Phe Glu Tyr Ala Gly Lys Asp Asn Tyr Cys Leu Gln Ile Asn
                    565                 570                 575

Pro Ala Ser Tyr Ile Asn Pro Asp His Leu Lys Tyr Phe Arg Phe Ile
                580                 585                 590

Gly Arg Phe Ile Ala Met Ala Leu Phe His Gly Lys Phe Ile Asp Thr
            595                 600                 605

Gly Phe Ser Leu Pro Phe Tyr Lys Arg Ile Leu Asn Lys Pro Val Gly
        610                 615                 620

Leu Lys Asp Leu Glu Ser Ile Asp Pro Glu Phe Tyr Asn Ser Leu Ile
    625                 630                 635                 640

Trp Val Lys Glu Asn Asn Ile Glu Glu Cys Gly Leu Glu Met Tyr Phe
                    645                 650                 655

Ser Val Asp Lys Glu Ile Leu Gly Glu Ile Lys Ser His Asp Leu Lys
                660                 665                 670

Pro Asn Gly Gly Asn Ile Leu Val Thr Glu Glu Asn Lys Glu Glu Tyr
            675                 680                 685

Ile Arg Met Val Ala Glu Trp Arg Leu Ser Arg Gly Val Glu Glu Gln
        690                 695                 700

Thr Gln Ala Phe Phe Glu Gly Phe Asn Glu Ile Leu Pro Gln Gln Tyr
    705                 710                 715                 720

Leu Gln Tyr Phe Asp Ala Lys Glu Leu Glu Val Leu Leu Cys Gly Met
                    725                 730                 735

Gln Glu Ile Asp Leu Asn Asp Trp Gln Arg His Ala Ile Tyr Arg His
                740                 745                 750

Tyr Thr Arg Thr Ser Lys Gln Ile Met Trp Phe Trp Gln Phe Val Lys
            755                 760                 765

Glu Ile Asp Asn Glu Lys Arg Met Arg Leu Leu Gln Phe Val Thr Gly
        770                 775                 780
```

```
Thr Cys Arg Leu Pro Val Gly Gly Phe Ala Asp Leu Met Gly Ser Asn
785                 790                 795                 800

Gly Pro Gln Lys Phe Cys Ile Glu Lys Val Gly Lys Glu Asn Trp Leu
                805                 810                 815

Pro Arg Ser His Thr Cys Phe Asn Arg Leu Asp Leu Pro Tyr Lys
                820                 825                 830

Ser Tyr Glu Gln Leu Lys Glu Lys Leu Leu Phe Ala Ile Glu Glu Thr
                835                 840                 845

Glu Gly Phe Gly Gln Glu
            850

<210> SEQ ID NO 5
<211> LENGTH: 21
<212> TYPE: DNA
<213> ORGANISM: Artificial Sequence
<220> FEATURE:
<223> OTHER INFORMATION: PCR Primer

<400> SEQUENCE: 5
atgggtagcc tcaccatgaa a                                            21

<210> SEQ ID NO 6
<211> LENGTH: 21
<212> TYPE: DNA
<213> ORGANISM: Artificial Sequence
<220> FEATURE:
<223> OTHER INFORMATION: PCR Primer

<400> SEQUENCE: 6
ttactcttgt ccaaatcctt c                                            21

<210> SEQ ID NO 7
<211> LENGTH: 156
<212> TYPE: PRT
<213> ORGANISM: Homo sapiens

<400> SEQUENCE: 7

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Arg Gly Gly Ala Lys Lys Arg
65                  70                  75                  80

Lys Lys Lys Ser Tyr Thr Thr Pro Lys Lys Asn Lys His Lys Arg Lys
                85                  90                  95

Lys Val Lys Leu Ala Val Leu Lys Tyr Tyr Lys Val Asp Glu Asn Gly
            100                 105                 110

Lys Ile Ser Arg Leu Arg Arg Glu Cys Pro Ser Asp Glu Cys Gly Ala
        115                 120                 125

Gly Val Phe Met Ala Ser His Phe Asp Arg His Tyr Cys Gly Lys Cys
    130                 135                 140

Cys Leu Thr Tyr Cys Phe Asn Lys Pro Glu Asp Lys
145                 150                 155
```

<210> SEQ ID NO 8
<211> LENGTH: 76
<212> TYPE: PRT
<213> ORGANISM: Homo sapiens

<400> SEQUENCE: 8

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 9
<211> LENGTH: 471
<212> TYPE: DNA
<213> ORGANISM: Homo sapiens

<400> SEQUENCE: 9
atgcagattt tcgtgaaaac ccttacgggg aagaccatca ccctcgaggt tgaaccctcg      60
gatacgatag aaaatgtaaa ggccaagatc caggataagg aaggaattcc tcctgatcag     120
cagagactga tctttgctgg caagcagctg aagatggacg tactttgtc tgactacaat     180 attcaaaagg agtctactct tcatcttgtg ttgagacttc gtggtggtgc taagaaaagg     240
aagaagaagt cttacaccac tcccaagaag aataagcaca agagaaagaa ggttaagctg     300
gctgtcctga atattataa ggtggatgag aatggcaaaa ttagtcgcct cgtcgagag      360 tgcccttctg atgaatgtgg tgctgggtg tttatgcaa gtcactttga cagacattat     420
tgtggcaaat gttgtctgac ttactgtttc aacaaaccag aagacaagta a              471

<210> SEQ ID NO 10
<211> LENGTH: 3177
<212> TYPE: DNA
<213> ORGANISM: Homo sapiens

<400> SEQUENCE: 10
atgtccagct cgccgctgtc caagaaacgt cgcgtgtccg ggcctgatcc aaagccgggt      60
tctaactgct cccctgccca gtccgtgttg tccgaagtgc cctcggtgcc aaccaacgga     120
atggccaaga acggcagtga agcagacata gacgagggcc tttactcccg gcagctgtat     180
gtgttgggcc atgaggcaat gaagcggctc cagacatcca gtgtcctggt atcaggcctg     240
cggggcctgg gcgtggagat cgctaagaac atcatccttg gtggggtcaa ggctgttacc     300
ctacatgacc agggcactgc ccagtgggct gatctttcct cccagttcta cctgcgggag     360
gaggacatcg gtaaaaaccg gccgaggta tcacagcccc gcctcgctga gctcaacagc     420
tatgtgcctg tcactgccta cactggaccc ctcgttgagg acttccttag tggttccag     480 gtggtggtgc tcaccaacac cccctggag gaccagctgc gagtgggtga gttcgtcac     540 aaccgtggca tcaagctggt ggtggcaggc acgcgggcc tgtttggca gctcttctgt     600 gactttggag aggaaatgat cctcacagat tccaatgggg agcagccact cagtgctatg     660
gtttctatgg ttaccaagga caaccccggt gtggttacct gcctggatga ggcccgacac     720
gggtttgaga gcggggactt tgtctccttt tcagaagtac agggcatggt tgaactcaac     780

-continued

```
ggaaatcagc ccatggagat caaagtcctg ggtccttata cctttagcat ctgtgacacc      840
tccaacttct ccgactacat ccgtggaggc atcgtcagtc aggtcaaagt acctaagaag      900
attagcttta atccttggt ggcctcactg gcagaacctg actttgtggt gacggacttc       960
gccaagtttt ctcgccctgc ccagctgcac attggcttcc aggccctgca ccagttctgt     1020
gctcagcatg gccggccacc tcggcccgc aatgaggagg atgcagcaga actggtagcc      1080
ttagcacagg ctgtgaatgc tcgagccctg ccagcagtgc agcaaaataa cctgacgag      1140 gacctcatcc ggaagctggc atatgtggct gctgggatc tggcacccat aaacgccttc      1200
attgggggcc tggctgccca ggaagtcatg aaggcctgct ccgggaagtt catgcccatc     1260
atgcagtggc tatactttga tgcccttgag tgtctccctc aggacaaaga ggtcctcaca     1320
gaggacaagt gcctccagcg ccagaaccgt tatgacgggc aagtggctgt gtttggctca     1380
gacctgcaag agaagctggg caagcagaag tatttcctgg tgggtgcggg ggccattggc     1440
tgtgagctgc tcaagaactt tgccatgatt gggctgggct gcggggaggg tggagaaatc     1500
atcgttacag acatggacac cattgagaag tcaaatctga atcgacagtt tcttttccgg     1560
ccctgggatg tcacgaagtt aaagtctgac acggctgctg cagctgtgcg ccaaatgaat     1620
ccacatatcc gggtgacaag ccaccagaac cgtgtgggtc ctgacacgga gcgcatctat     1680
gatgacgatt ttttccaaaa cctagatggc gtggccaatg ccctggacaa cgtggatgcc     1740
cgcatgtaca tggaccgccg ctgtgtctac taccggaagc cactgctgga gtcaggcaca     1800
ctgggcacca aaggcaatgt gcaggtggtg atccccttcc tgacagagtc gtacagttcc     1860
agccaggacc cacctgagaa gtccatcccc atctgtaccc tgaagaactt ccctaatgcc     1920
atcgagcaca ccctgcagtg ggctcgggat gagtttgaag gcctcttcaa gcagccagca     1980
gaaaatgtca accagtacct cacagacccc aagtttgtgg agcgaacact gcggctggca     2040
ggcactcagc ccttggaggt gctggaggct gtgcagcgca gctggtgct gcagcgacca     2100 cagacctggg ctgactgcgt gacctgggcc tgccaccact ggcacaccca gtactcgaac     2160
aacatccggc agctgctgca aacttccct cctgaccagc tcacaagctc aggagcgccg     2220
ttctggtctg ggcccaaacg ctgtccacac ccgctcacct ttgatgtcaa caatcccctg     2280
catctggact atgtgatggc tgctgccaac ctgtttgccc agacctacgg gctgacaggc     2340
tctcaggacc gagctgctgt ggccacattc ctgcagtctg tgcaggtccc cgaattcacc     2400
cccaagtctg gcgtcaagat ccatgtttct gaccaggagc tgcagagcgc caatgcctct     2460
gttgatgaca tcgtctaga ggagctcaaa gccactctgc ccagcccaga caagctccct     2520
ggattcaaga tgtacccat tgactttgag aaggatgatg acagcaactt tcatatggat     2580
ttcatcgtgg ctgcatccaa cctccgggca gaaaactatg acattccttc tgcagaccgg     2640
cacaagagca agctgattgc agggaagatc atcccagcca ttgccacgac cacagcagcc     2700
gtggttggcc ttgtgtgtct ggagctgtac aaggttgtgc aggggcaccg acagcttgac     2760
tcctacaaga atggtttcct caacttggcc ctgcctttct ttggtttctc tgaacccctt     2820
gccgcaccac gtcaccagta ctataaccaa gagtggacat tgtgggatcg ctttgaggta     2880
caagggctgc agcctaatgg tgaggagatg accctcaaac agttcctcga ctatttaag     2940 acagagcaca aattagagat caccatgctg tcccagggcg tgtccatgct ctattccttc     3000
ttcatgccag ctgccaagct caaggaacgg ttggatcagc cgatgacaga gattgtgagc     3060
cgtgtgtcga agcgaaagct gggccgccac gtgcgggcgc tggtgcttga gctgtgctgt     3120
```

-continued

```
aacgacgaga gcggcgagga tgtcgaggtt ccctatgtcc gatacaccat ccgctga      3177

<210> SEQ ID NO 11
<211> LENGTH: 444
<212> TYPE: DNA
<213> ORGANISM: Homo sapiens

<400> SEQUENCE: 11
atggcgctga aacggattaa taaggaactt agtgatttgg cccgtgaccc tccagcacaa     60
tgttctgcag gtccagttgg agatgacatg tttcattggc aagccacaat tatgggacct    120
aatgacagcc catatcaagg tggtgtattc tttttgacaa ttcatttcc tacagactac     180 cccttcaaac cacctaaggt tgcatttaca acaagaattt atcatccaaa tattaacagt    240
aatggcagca tttgtcttga tattctaaga tcacagtggt ctcctgcttt aactatttct    300
aaagttcttt tatccatttg ttcactgcta tgtgatccaa acccagatga cccccctagtg   360 ccagagattg cacggatcta taaaacagac agagacaagt acaacagaat atctcgggaa    420
tggactcaga agtatgccat gtga                                           444

<210> SEQ ID NO 12
<211> LENGTH: 20
<212> TYPE: DNA
<213> ORGANISM: Artificial Sequence
<220> FEATURE:
<223> OTHER INFORMATION: PCR Primer

<400> SEQUENCE: 12
gtctgacagt ggatcacaac                                                 20

<210> SEQ ID NO 13
<211> LENGTH: 21
<212> TYPE: DNA
<213> ORGANISM: Artificial Sequence
<220> FEATURE:
<223> OTHER INFORMATION: PCR Primer

<400> SEQUENCE: 13
ccattcatgg tgcaagttct c                                               21

<210> SEQ ID NO 14
<211> LENGTH: 45
<212> TYPE: DNA
<213> ORGANISM: Artificial Sequence
<220> FEATURE:
<223> OTHER INFORMATION: PCR Primer

<400> SEQUENCE: 14
ggctacccag aagtcatacc gcttttaatc gcctggacct gccac                     45

<210> SEQ ID NO 15
<211> LENGTH: 45
<212> TYPE: DNA
<213> ORGANISM: Artificial Sequence
<220> FEATURE:
<223> OTHER INFORMATION: PCR Primer

<400> SEQUENCE: 15
gtggcaggtc caggcgatta aaagcggtat gacttctggg tagcc                     45
```